US010139404B2

(12) United States Patent
Pouzet et al.

(10) Patent No.: US 10,139,404 B2
(45) Date of Patent: Nov. 27, 2018

(54) CONTROL MARKER FOR IMPLEMENTING ANALYSIS METHODS ON SPOTS

(71) Applicant: BIO-RAD EUROPE GMBH, Basel (CH)

(72) Inventors: Agnes Roseline Claude Pouzet, Saint Cyr l'Ecole (FR); Vincent Doury, Ville d'Avray (FR); Laurent Emmanuel Fournier, Versailles (FR); Christophe Rene Roger Vedrine, Courbevoie (FR)

(73) Assignee: BIO-RAD EUROPE GMBH, Basel (CH)

( * ) Notice: Subject to any disclaimer, the term of this patent is extended or adjusted under 35 U.S.C. 154(b) by 0 days.

(21) Appl. No.: 15/302,512

(22) PCT Filed: Apr. 8, 2015

(86) PCT No.: PCT/EP2015/057639
§ 371 (c)(1),
(2) Date: Oct. 7, 2016

(87) PCT Pub. No.: WO2015/155254
PCT Pub. Date: Oct. 15, 2015

(65) Prior Publication Data
US 2017/0030902 A1  Feb. 2, 2017

(30) Foreign Application Priority Data
Apr. 9, 2014 (FR) ...................... 14 53169

(51) Int. Cl.
*G01N 1/10* (2006.01)
*G01N 33/543* (2006.01)
(Continued)

(52) U.S. Cl.
CPC ... *G01N 33/54373* (2013.01); *G01N 21/6428* (2013.01); *G01N 21/6452* (2013.01);
(Continued)

(58) Field of Classification Search
CPC ............... G01N 33/582; G01N 33/581; G01N 33/54373; G01N 33/558; G01N 21/6452;
(Continued)

(56) References Cited

U.S. PATENT DOCUMENTS 5,451,504 A * 9/1995 Fitzpatrick ........... G01N 33/558
435/7.2
2002/0090649 A1 * 7/2002 Chan .................... B01J 19/0046
435/7.1
(Continued)

FOREIGN PATENT DOCUMENTS

| WO | WO 2015/150583 | 10/2015 |
| WO | WO 2015/155248 | 10/2015 |
| WO | WO 2015/155255 | 10/2015 |

OTHER PUBLICATIONS

Written Opinion in International Application No. PCT/EP2015/057639, dated May 19, 2015, pp. 1-6.

*Primary Examiner* — Hoa Pham
(74) *Attorney, Agent, or Firm* — Saliwanchik, Lloyd & Eisenschenk

(57) ABSTRACT

The present invention relates to the use of a control marker for implementing analysis methods on spots, in particular in the context of multiplex analyses. The present invention thus relates to solid supports containing said control marker, their preparation method and their use in analysis methods. The present invention makes it possible to verify the presence, location and/or integrity of the spots at the end of the analysis method, and thus to secure the obtained results while guaranteeing that the yielded result indeed results from a present, intact and localized spot.

5 Claims, 4 Drawing Sheets

(51) Int. Cl.
*G01N 21/64* (2006.01)
*G01N 33/58* (2006.01)

(52) U.S. Cl.
CPC ......... *G01N 33/581* (2013.01); *G01N 33/582* (2013.01); *B01J 2219/00576* (2013.01); *B01J 2219/00659* (2013.01); *B01J 2219/00693* (2013.01); *G01N 2021/6439* (2013.01); *G01N 2458/30* (2013.01)

(58) Field of Classification Search
CPC ........ G01N 21/6428; G01N 2021/6439; Y02E 10/563; B01J 2219/00693
USPC .......................... 356/432–440, 335–343, 73
See application file for complete search history.

(56) References Cited

U.S. PATENT DOCUMENTS

| | | | |
|---|---|---|---|
| 2006/0063197 A1 | 3/2006 | Anderson et al. | |
| 2007/0114362 A1* | 5/2007 | Feng | G01N 21/6428 250/208.1 |
| 2010/0296727 A1* | 11/2010 | Stern | G01N 21/6452 382/154 |
| 2011/0212848 A1* | 9/2011 | Duffy | G01N 33/54306 506/9 |
| 2011/0256549 A1* | 10/2011 | Gaylord | C08G 61/02 435/7.1 |
| 2012/0196767 A1 | 8/2012 | Cooney et al. | |

* cited by examiner

CONTROL MARKER FOR IMPLEMENTING ANALYSIS METHODS ON SPOTS

CROSS-REFERENCE TO RELATED APPLICATION

This application is the U.S. national stage application of International Patent Application No. PCT/EP2015/057639, filed Apr. 8, 2015.

FIELD OF THE INVENTION

The present invention relates to the use of a control marker for implementing analysis methods on spots, in particular in the context of multiplex analyses. The present invention thus relates to solid supports containing said control marker, their preparation method and their use in analysis methods. The present invention makes it possible to verify the presence, location and/or integrity of the spots at the end of the analysis method, and thus to secure the obtained results while guaranteeing that the yielded result indeed results from a present, intact and localized spot.

BACKGROUND OF THE INVENTION

A multiplex analysis method allows the simultaneous detection of the potential presence of several analytes within a same sample. A multiplex analysis method is typically implemented using a solid support comprising spots, for example a microplate comprising spots in each well, the spots each being intended to detect an analyte or to serve as a control.

It is clear for one skilled in the art that one risk related to spot technology is the absence of deposit, the elimination or deterioration of several spots during the preparation method for the solid support, in particular a microplate, or during the implementation of the analysis method using said solid support. The device for depositing samples or reagents may indeed accidentally come into contact with one or several spots, thereby altering their surface, for example by forming a striation in one or several spots, or by pulling out all or part of one or more spots.

For example, in the article by Bastarache et al. (*Accuracy and Reproducibility of a multiplex Immunoassay platform: a validation study, J. Immunol Methods*, Mar. 31, 2011, 367 (1-2) 33-39), flaws are presented that were observed at the end of testing on the light signal, such as spot irregularities, the presence of comas that cause the contamination of one spot by a neighboring spot and the absence of expected signal at the theoretical location of the spot.

Yet when a negative result is rendered at the end of the analysis method, this result must result from the absence of the analyte to be detected in the sample, and not from an absence or a deterioration of the detection spot of the corresponding analyte. Securing analysis methods is crucial, in particular for their use in diagnostics in humans, for example to verify the absence of viral or bacterial contamination of a blood sample for transfusion purposes.

The manufacture of a solid support for a spot analysis consists of depositing, on the surface of the solid support, solutions comprising a capture ligand of the analyte to be detected, so as to form spots. The quality of the solid support is next verified at the end of the manufacturing of the solid support, so as to keep only the solid supports having intact and well-formed spots.

Thus, document US2006/0063197 describes the use of a fluorophore in the deposition solution intended to form the spots of a DNA microarray. The fluorophore is used to verify the quality of each spot at the end of the preparation method for the DNA microarray. Furthermore, only a weak residual fluorescence signal is detected at the spots before adding the substrate, during the implementation of an ELISA test.

Document WO2012/142397 examines flux issues in microfluidic apparatuses containing DNA microarrays and describes a DNA microarray assembly comprising an array chamber with an inlet for the sample at a first end, a DNA microarray and an outlet for the sample at a second end connected to a waste chamber, the area transverse to the first end of the array chamber being wider than that at the second end. This document also describes a method for verifying the manufacturing quality of a DNA microarray, by measuring the fluorescence emitted by an internal quality control fluorophore at the spots of an array and encoding the information relative to each spot of the array in a barcode, a memory device or by radiofrequency identification, this information thus encoded being associated with the DNA microarray.

Furthermore, during the implementation of a multiplex analysis method, the signal corresponding to the analyte to be detected can be detected at a theoretical reading grid. This theoretical reading grid is generally defined at the end of the multiplex analysis method, from the signal detected at a spot serving as a positive control. However, in light of the reading scales, any shift in the positioning of the spots during the manufacture of the solid support and/or in the positioning of the solid support in the device for detecting the signal relative to the theoretical reading grid causes a shift in the actual positioning of the spots relative to the theoretical reading grid and therefore affects the detection sensitivity of the analytes.

There is therefore still a need for solutions to secure the results obtained at the end of an analysis method on spots, in particular by making it possible to verify the presence, location and/or integrity of the spots at the end of the analysis method and/or by making it possible to optimize the detection of analytes, for example by improving the detection sensitivity of the analytes.

DETAILED DESCRIPTION OF THE INVENTION

The present invention is based on revealing control markers that may be deposited, to form spots on a solid support, at the same time as specific capture ligands of the analytes to be detected in a sample, these control markers being capable of producing a signal at the end of an analysis method implemented using said solid support, interfering negligibly or not at all with the detection of the analytes. The control markers according to the invention thus make it possible to verify the presence, location and/or integrity of the spots at the end of an analysis method. These control markers are qualified here as "resistant control markers".

The expressions "analysis method" and "method for detecting at least one analyte" are synonymous here.

The terms "produce", "product" or "production" apply to any type of signal, and in particular any type of electromagnetic radiation, whether it involves a radioactive signal, a light emission or absorbance.

When the detected signal is a fluorescence luminescence signal, the "produced signal" is in particular an "emitted signal", and "produce a signal" and "production of a signal" then mean "emit a signal" and "emission of a signal", respectively.

"Detection of at least one analyte" (or "detect at least one analyte") means, within the present application, detection of the presence (or detect the presence) of said analyte(s) and/or quantification of said analyte(s) (or quantify said analyte(s)).

"End of an analysis method" means, within the meaning of the invention, after the spots have been placed in the presence of the sample to be analyzed, a ligand or ligands for detecting an analyte, if applicable at least one (first) reporter of a detection marker coupled to a detection ligand of an analyte and, if applicable, at least one (second) reporter of a detection marker coupled to said first reporter.

Surprisingly, the inventors have thus shown resistant control markers that can be fixed on a solid support, that do not interfere with the analysis method itself and that remained completely detectable (in particular because they remain at least partially fixed on the solid support) after implementing different steps of the analysis method. When the signal produced by the resistant control marker at the end of the analysis method makes it possible to define a spot meeting the quality criteria of a spot, in particular presence, location and/or integrity, the signal corresponding to an analyte can then be detected at this spot. In particular, the resistant control markers according to the invention can be used in an analysis method in which the presence of at least one analyte is detected by a signal emitted by chemiluminescence, preferably via the reaction of a peroxidase enzyme with a luminol substrate and/or an analogue of luminol, for example isoluminol, and/or one of their derivatives.

The resistant control markers according to the invention have the advantage of making it possible to control spots of a solid support at the end of an analysis method, and not only at the end of the preparation method of said solid support.

Thus, the present invention makes it possible to guarantee the results for the user. In particular, the present invention makes it possible to guarantee that a negative result indeed results from the absence of the analyte in a sample and not for example from an absence of spot or a shift in the reading of the spot. In other words, the present invention makes it possible to eliminate false negative results (also called "false negatives") related to a flaw of a spot (i.e., a spot not compliant with the quality criteria) and/or a reading flaw of a spot at the end of the analysis method and that are not detectable in the multiplex analysis methods traditionally used, in which the reading grid is adjusted theoretically, for example on the signal emitted by a positive control spot. The present invention also makes it possible to guarantee that a positive result indeed results from the presence of the analyte in a sample. For example, a signal may be detected corresponding to the marker of an analyte in the theoretical location of a spot (as defined by a theoretical reading grid, for example adjusted on the signal emitted by a control spot), whereas there is no spot in that location; such a falsely positive result (also called "false positive") would then occur during the implementation of a traditional analysis method; by using a resistant control marker according to the invention in the spots of the solid support, no signal corresponding to said resistant control marker will be detected at this theoretical location of a spot and the analysis method will lead to an absence of result rendered, despite the detection of a signal corresponding to the marker of the analyte in that location.

Another advantage of the present invention lies in the fact that the resistant control markers make it possible to define the reading grid at the end of the analysis method. Yet there may be differences between a theoretical reading grid defined according to the physical parameters of the solid support and that defined at the end of an analysis method using said solid support. These differences may for example result from a shift between the expected theoretical spot grid and the grid actually obtained at the end of the analysis method (one or several spots); this shift is thus corrected by the device described in the present application. It is thus more reliable to define the reading grid of a solid support at the end of the analysis method, preferably with the same detection device as that used to detect the signal produced by the detection marker of at least one detection ligand of an analyte, and preferably concomitantly. Thus, the resistant control markers according to the invention also make it possible to secure the results of an analysis method on spots, by improving the sensitivity of the analyte detection owing to the definition of a reading grid to detect analytes from the location of the spots detected at the end of the analysis method.

Lastly, the preparation of a solid support whereof the spots comprise a resistant control marker according to the invention is simple to do and does not add any additional steps, the resistant control marker for example being able to be simply mixed with the compound of interest, such as a capture ligand, in the solution to be deposited to form the spot.

The present invention in particular relates to a solid support for a secure detection of at least one analyte in a sample, whereof at least one spot intended to detect an analyte comprises at least one resistant control marker and at least one capture ligand of an analyte, a method for preparing such a solid support and a secure detection method for at least one analyte in at least one sample using said solid support.

"At least one", within the meaning of the present application, refers to one or several, several in particular meaning two, three, four, five, six, seven, eight, nine, ten, eleven, twelve, thirteen, fourteen, fifteen or more than fifteen. Similarly, in the present application, "at least" means, x or more than x, and in particular x+1, x+2, x+3, x+4, etc., "x" being an integer greater than or equal to 2, for example 2 or 3.

One particularly preferred analysis method according to the invention is a multiplex analysis method.

The present invention also relates to a method for selecting a resistant control marker, as well as the use of at least one resistant control marker in at least one spot intended to detect an analyte to secure a method for detecting at least one analyte in a sample.

The present invention also provides an appropriate device for improved detection of at least one analyte in a sample.

Sample

The sample to be analyzed is preferably a biological sample.

The biological sample may be a biological fluid, such as a sample of blood, blood derivatives (such as plasma or serum), urine, cerebrospinal fluid, saliva or combinations thereof, or a tissue sample, such as a tissue obtained by biopsy, a cell, a set of cells, a plant extract, or combinations thereof.

A blood derivative refers to any product, in particular fluid, obtained from a blood sample.

The sample to be analyzed may also be a culture medium and/or a culture supernatant.

Before being analyzed, the sample may undergo one or several prior treatment steps, such as dilution, centrifugation, heat treatment, cell lysis, solubilization, and denaturation (for example by one or several chaotropic agents, one or several reducing agents and/or by heating), extraction, PCR (Polymerase Chain Reaction), addition of an unmarked detection ligand or combinations thereof. The addition of an unmarked detection ligand is in particular useful to implement a neutralization test.

The sample may also be a mixture of at least two samples that may be of the same nature or different natures.

Examples of mixtures of samples of different natures are a mixture of blood and urine, a mixture of blood and plasma, a mixture of serum and plasma, or a mixture of blood, serum and plasma.

One preferred sample according to the invention is a sample or mixture of samples of blood and/or blood derivatives (in particular plasma and/or serum).

Analyte

An analyte to be detected in a sample may be any type of compound, natural or synthetic, that one wishes to detect and/or quantify in a sample.

An analyte may for example be a protein, a peptide, a glycoprotein, a carbohydrate, a cell, an organelle, a virus or a nucleic acid.

The cell may be an animal cell, a plant cell, a bacteria cell, a protozoa, a metazoan cell, a yeast cell or a fungus cell.

A nucleic acid designates a polymer of nucleotides linked by phosphodiester bonds, such as a deoxyribonucleic acid (DNA), a ribonucleic acid (RNA) or an analogue thereof, such as phosphorothioates or thioesters, in single-strand or double-stranded form.

The analyte or at least one of the analytes is thus for example chosen from the group consisting of an antigen, an antibody, an antibody fragment, a hapten, a hormone, a hormone receptor, an enzyme, or a nucleic acid.

The analyte(s) are preferably selected from the group consisting of an antigen, an antibody, an antibody fragment, a hapten, a hormone, a hormone receptor and an enzyme.

Within the meaning of the present application, "antigen" refers to a natural, recombinant or synthetic molecule recognized by antibodies or cells of the immune system and capable, when it is presented under appropriate conditions to the immune system of a host, of inducing an immune response.

An antigen may be a molecule, in particular a polypeptide, comprising or consisting of at least one epitope that may be linear or conformational. The term "linear epitope" refers to a polypeptide, in particular a peptide, comprising or generally consisting of 3 to 15 amino acids, more generally 5 to 15 amino acids, preferably at least 6, 8, 10 or 12 amino acids, capable of binding to an antibody molecule against said antigen. The term "conformational epitope" refers to a three-dimensional structure recognized by an antibody and determined by the juxtaposition of several amino acids in space, which may be noncontiguous in the peptide sequence of the protein (or polypeptide) against which this antibody is directed, but which, due to the folding of the polypeptide chain, find themselves close to one another in space, and can thus form a pattern that may be recognized by an antibody.

An antigen within the meaning of the present invention is for example a protein (in particular a native protein or a recombinant protein), a peptide (for example, a synthetic peptide), a glycoprotein, a carbohydrate or a lipid; said peptide may or may not be associated with a carrier molecule.

A "carrier molecule" in particular refers to a protein or carbohydrate carrier molecule, in particular a carrier protein. A carrier molecule may be a polypeptide (in particular protein or a peptide), which may or may not be natural (for example, a recombinant protein or a synthetic peptide), a functionalized polymer (such as dextran, polysaccharide or polylysine), a mixed copolymer (in particular a copolymer of different amino acids, for example a lysine-tyrosine copolymer). The carrier molecule may be an antibody (in particular a monoclonal antibody or a polyclonal antibody), for example an immunoglobulin (also called Ig).

One example carrier molecule or protein is BSA (bovine serum albumin).

"Hapten" in the present application refers to a molecule with a low molecular weight capable of being recognized by the immune system, but which is immunogenic only when it is coupled to a carrier molecule.

An analyte is preferably a compound making it possible to diagnose a condition in a subject, which may or may not be pathological, or to diagnose the risks of developing a condition, which may or may not be pathological. An example of a non-pathological condition is a pregnancy.

The subject may be a human, a non-human animal or a plant. The non-human animal is preferably a mammal, such as a cat, dog, monkey, rabbit, mouse or rat.

The term "human" is used broadly and in particular designates a man or a woman of any age, such as an infant, a child, an adolescent, an adult or any elderly person.

In one preferred embodiment, at least one analyte is chosen from among an antigen or an antibody.

When the analyte or one of the analytes is an antigen, it is preferably an antigen making it possible to diagnose an infection, for example an infection caused by a virus, a bacteria, a fungus, a protozoa or a metazoan.

When the analyte or one of the analytes is an antibody, it is preferably an antibody making it possible to diagnose an infection, for example an infection caused by a virus, a bacteria, a fungus, a protozoa or a metazoan.

In another preferred embodiment, at least one analyte is a nucleic acid.

In another preferred embodiment, the analyte(s) are not nucleic acids.

When the analyte or one of the analytes is a nucleic acid, it is preferably a nucleic acid making it possible to diagnose an infection, for example an infection caused by a virus, a bacteria, a fungus, a protozoa or a metazoan.

Typically, this may involve one or several antigens and/or one or several antibodies and/or one or several specific nucleic acids of:

a virus, such as HIV (Human Immunodeficiency Virus), in particular HIV-1 or HIV-2, HBV (Hepatitis B Virus), HCV (Hepatitis C Virus), HPV (Human Papilloma Virus), HTLV (Human T-Lymphotropic Virus), in particular HTLV-I or HTLV-II, a parasite, such as a parasite that may cause toxoplasmosis (in particular *Toxoplasma gondii*), malaria (in particular a parasite of the *Plasmodium* genus, for example *Plasmodium falciparum, Plasmodium vivax, Plasmodium ovale, Plasmodium malariae* or *Plasmodium knowlesi*) or Chagas disease (in particular *Trypanosoma cruzi*) in humans or non-human animals, or a bacteria, such as a bacteria able to cause syphilis (*Treponema pallidum*) or Lyme disease (in particular a bacteria from the *Borrelia* genus) in humans or non-human animals.

"Parasite" here refers to a metazoan or a protozoa acting as parasite with respect to a body and causing parasitosis A parasite within the meaning of the invention is therefore not a virus, a bacteria or a fungus.

The analyte or at least one of the analytes may also be a marker for disease, such as a marker of a cardiovascular disease or a diabetes marker, a marker of the evolution of the disease, such as hepatitis, a marker of the evolution of an infection caused by a virus, a bacteria, a fungus or a parasite, a marker of resistance to a treatment, for example to an antiviral treatment, an antibiotic treatment or a cancer treatment.

Several (for example, two, three, four, five, six, seven, eight, nine, ten, eleven, twelve, thirteen, fourteen, fifteen or more than fifteen) analytes as described in the present application may be detected simultaneously in a same sample or a same mixture of samples during a multiplex analysis method. This may make it possible to diagnose, in a same sample or a same mixture of samples, one or several infections or diseases, the evolution of an infection or disease, a condition (pathological or not), a risk of developing a condition (pathological or not) or a marker of resistance to a treatment in a subject.

The analytes detected during a multiplex analysis method may be of the same nature (for example only antibodies, only antigens or only nucleic acids) or of different natures (for example, at least one antigen and at least one antibody).

Capture Ligand

A capture ligand is a specific molecule of a compound of interest.

A capture ligand is preferably specific to an analyte to be detected in a sample. It generally involves an antibody, an antigen, a peptide, a carbohydrate, a lipid or a nucleic acid.

In one advantageous embodiment, the capture ligand is not a nucleic acid. The capture ligand(s) are for example selected from the group consisting of an antibody, an antigen, a peptide, a carbohydrate and a lipid.

A capture ligand is fixed to the surface of a solid support at a spot.

In one preferred embodiment, the capture ligand(s) is (are) an antibody, an antigen or a nucleic acid.

In one more preferred embodiment, the capture ligand(s) are an antibody or an antigen.

When the capture ligand, or one of the capture ligands, is an antibody, it for example involves a monoclonal antibody or a polyclonal antibody.

Detection Ligand

A detection ligand is a specific molecule of a compound of interest. It in particular makes it possible to detect a compound of interest fixed to a capture ligand.

A detection ligand of an analyte is specific to an analyte to be detected in a sample. It in particular makes it possible to detect an analyte fixed to a capture ligand.

A detection ligand may be an antibody, an antigen, a peptide, a carbohydrate, a lipid or a nucleic acid. It is preferably an antibody or an antigen.

In another embodiment, the or one of the detection ligand(s) is (are) a nucleic acid.

In another embodiment, the detection ligand is not a nucleic acid. The detection ligand(s) are for example selected from the group consisting of an antibody, an antigen, a peptide, a carbohydrate and a lipid.

When the detection ligand, or one of the detection ligands, is an antibody, it for example involves a monoclonal antibody or a polyclonal antibody.

The detection ligand or one of the detection ligands is preferably a marked detection ligand, i.e., a detection ligand to which a detection marker (which may for example be biotin or a peroxidase) is attached. The detection marker is attached (i.e., coupled) to the detection ligand covalently or non-covalently, preferably covalently. The detection ligand or one of the detection ligands may be coupled to a direct or indirect detection marker.

When the detection ligand is not marked, its detection may be done by using a specific marked antibody of said detection ligand.

A detection ligand may be identical to the used capture ligand or one of the used capture ligands, with the exception of any presence of a detection marker, and/or bind to the analyte to which it is specific at the same zone as that bonded by the capture ligand or one of the capture ligands, in particular when the analyte to which it is specific is in the form of a complex having at least two identical bonding zones. Thus, when one of the analytes that one wishes to detect is an antibody, it is possible to use, as capture ligand and detection ligand of said analyte, a same specific antigen of said antibody or two different antigens including at least one shared zone (at least one shared epitope) allowing the recognition by the bivalent antibody.

A capture ligand and a detection ligand may also be specific to separate zones at an analyte.

In one particular embodiment, a detection ligand and a capture ligand (for example, antibodies) specific to a same analyte (for example, an antigen) do not bond to the same location on said analyte. For example, the detection ligand can bond to a zone of said analyte to which it is specific that is separated from the bonding zone of the capture ligand, for example so as to avoid competition of the capture ligand and the detection ligand with respect to the compound to which they are specific, due to a steric hindrance.

Detection Marker of the Detection Ligand

A detection marker coupled to the detection ligand may be a direct marker or an indirect marker.

A direct marker is a marker whose signal can be detected directly, i.e., without requiring the prior addition of a reporter.

A direct marker is for example selected from the group consisting of a radioisotope, a fluorophore, a heavy element from the periodic table such as a lanthanide, a luminescent compound, a transition metal such as ruthenium, a chromogenic, and colored, fluorescent or luminescent nanoparticles.

A "luminescent" compound may be an electroluminescent compound, a thermoluminescent compound or a chemiluminescent compound. In one preferred embodiment, the luminescent compound is a chemiluminescent compound.

One example luminescent compound (more specifically, thermoluminescent compound) that may be used as a direct marker consists of silica nanoparticles comprising (for example doped with) molecules of a dioxetane compound, in particular the 1,2-dioxetane compound, or a derivative of a dioxetane compound, for example a derivative of 1,2-dioxetane.

An indirect marker is a marker for which detection of the signal requires the prior addition of a reporter (also called first reporter) and, if said reporter itself is coupled to an indirect detection marker, the addition of a second reporter of the indirect detection marker coupled to said first reporter.

A reporter is a substrate of an indirect marker or a molecule specifically bonding to an indirect marker, said molecule itself being a direct or indirect marker or itself being coupled to a direct or indirect marker.

An indirect marker is for example selected from the group consisting of an enzyme, a ligand of a ligand-receptor pair, a receptor of a ligand-receptor pair, a hapten, an antigen and an antibody.

A ligand or a receptor of a ligand-receptor pair is for example biotin, an analogue of biotin, avidin, streptravidin, neutravidin or digoxigenin.

A preferred indirect marker according to the invention is an enzyme, preferably an enzyme producing a luminescent compound by reaction with a substrate.

The detection of the signal of an indirect marker requires the prior addition of a reporter of said indirect marker.

A reporter of an enzyme is for example a substrate of said enzyme.

A reporter of the biotin is, for example, avidin, streptavidin or neutravidin, preferably coupled with a direct marker or an indirect marker, such as an enzyme or a catalyst.

A reporter of the biotin is, preferably, coupled with a direct or indirect detection marker, such as an enzyme or a catalyst.

An example enzyme is peroxidase, for example horseradish peroxidase (HRP or POD), alkaline phosphatase or luciferase One preferred biotin reporter according to the invention is streptavidin coupled with a peroxidase, preferably horseradish peroxidase. The detection of the signal of the biotin then requires adding streptavidin coupled with the peroxidase, then adding the substrate of the peroxidase.

In this preferred embodiment, the detection ligand or one of the detection ligands is coupled to a direct or indirect detection marker selected from among a peroxidase enzyme or a biotin.

When the analyte is a nucleic acid, the detection marker or one of the detection markers may be detected by fluorescence, for example by using direct or indirect marking with a fluorophore, bioluminescence, preferably by chemiluminescence, for example by using direct marking with a luminescent compound or indirect marking with an enzyme, in particular a peroxidase, producing a luminescent compound by reaction with a substrate.

When the analyte is a compound of the protein type, the detection marker or one of the detection markers is preferably detected by luminescence, for example by using direct or indirect marking with a compound of the protein type, in particular a chemiluminescent compound or indirect marking with an enzyme as reporter producing a luminescent compound by reaction with a substrate.

In one particular embodiment of the invention, the detection marker or one of the detection markers used has, as substrate, luminol, isoluminol, an acridine, coelenterazine, dioxetane or peroxyoxalic compound, or one of their derivatives, and in particular a compound described in the publication Dodeigne C. et al (2000), *Talanta* 51, 415-439, "*Chemiluminescence as diagnostic tool. A review*".

In one particular embodiment, the detection marker or one of the detection markers used has, as substrate, luminol, an analogue of luminol, for example isoluminol, or one of their derivatives "Luminol" refers to 3-aminophthalhydrazide, also called 5-amino-2,3-dihydro-phthalazine-1,4-dione. The raw formula for luminol is $C_8H_7N_3O_2$. As an example, it is possible to use the ELISTAR ETA C Ultra ELISA (Cyanagen, Italy) substrate described in the examples.

"Isouminol" refers to 4-aminophthalhydrazide.

A derivative of luminol or an analogue of luminol is preferably a molecule obtained respectively from the luminol or the analogue of the luminol, through all possible modification(s) (for example, chemical and/or enzymatic). A derivative of luminol or an analogue of luminol is for example a substrate of a peroxidase enzyme, the reaction of said peroxidase enzyme with a derivative of the luminol or the analogue of the luminol making it possible to produce a chemiluminescent compound.

A derivative of the isoluminol may for example be aminoethylisoluminol (or AEI), aminoethylethylisoluminol (or AEEI), aminobutylisoluminol (or ABI), aminobutylethylisoluminol (or ABEI), aminopentylethylisoluminol (or APEI), aminohexylisoluminol (or AHI), aminohexylethylisoluminol (or AHEI), aminooctylmethylisoluminol (or AOMI) or aminooctylethylisoluminol (or AOEI), as described in the publication Dodeigne C. et al (2000), *Talanta* 51, 415-439, "*Chemiluminescence as diagnostic tool. A review*".

In one particular embodiment of the invention, the "luminol, analogue of the luminol (for example isoluminol), acridine, coelenterazine, dioxetane or peroxyoxalic compound, or one of their derivatives" may be contributed in the form of a composition (or formulation) comprising said luminol, acridine, coelenterazine, dioxetane or peroxyoxalic compound, or one of their derivatives.

Resistant Control Marker

The present invention is based on the use of one or several resistant control markers (for example, a mixture of resistant control markers) making it possible to control the quality of spot(s) present on the surface of a solid support, in particular the presence, location and/or integrity of the spot(s) present on the surface of a solid support, this control (or one of these controls) being able to be done at the end of the analysis method carried out.

A resistant control marker is a compound able to be detected, for example by producing a signal. The produced signal may for example be a radioactive signal or a light signal. It may also involve a control marker (for example, a colored control marker) that is detected by light absorption.

A light signal corresponds to the emission of a light, in particular in a given wavelength range.

A resistant control marker can for example be a marker emitting light by fluorescence, phosphorescent or luminescence, in particular electroluminescence, thermoluminescence or chemiluminescence.

When the or one of the resistant control markers is a marker emitting light by luminescence, it preferably emits light by chemiluminescence.

One preferred resistant control marker is a marker emitting light by fluorescence.

As its name indicates, a resistant control marker according to the invention is resistant.

"Resistant control marker" here refers to a marker whereof a signal is detected at the end of an analysis method. A resistant control marker is in particular a control marker that remains, in full or at least partially, fixed at a spot on the surface of a solid support, during the preparation method of the solid support and also during the analysis method implementing said support, and that is capable of producing a signal detectable at the end of the analysis method, i.e., including in the presence of a detection marker of a detection ligand of an analyte and/or one or several reporters in the case of one or several indirect detection markers.

In the expression "marker capable of producing a signal detectable at the end of the analysis method", "capable" means that the resistant control marker present in a spot produces a signal detectable at that spot at the end of the analysis method, when said analysis method has taken place with no deterioration of said spot.

The expressions "able to be detected", "whereof a signal is detected", "capable of producing a detectable signal" or "producing a detectable signal" at the end of the analysis mean, in particular in the case where the resistant control marker is a fluorophore, that the "detected signal" (the signal produced by the resistant control marker and measured on the imaging sensor at the corresponding pixel zone) minus (i.e., from which one subtracts) the mean signal of the surrounding pixels is around three standard deviations above the level of the surrounding pixel signals. When the detected signal minus the mean signal of the surrounding pixels reaches at least three standard deviations above the level of the signals of the surrounding pixels, said detected signal is qualified as "detectable signal".

A control marker within the meaning of the invention is thus resistant to the washing and incubation steps with the different reagents used during an analysis method, such as the detection ligand(s), the reporter(s), the substrate(s), the sample, one or several diluents.

In particular, a resistant control marker according to the invention is resistant to the use of the detection marker(s) of a detection ligand of an analyte, if applicable the (first) reporter of the detection marker(s) of a detection ligand of an analyte and if applicable the (second) reporter of the indirect marker coupled to said first reporter.

In one preferred embodiment, a resistant control marker according to the invention is resistant to the use of one or several enzymes, in particular an alkaline phosphatase and/or a peroxidase, and to the substrate(s) of said enzyme(s).

One preferred control marker according to the invention is resistant to the use of a substrate selected from the group consisting of luminol, isoluminol or one of their derivatives.

In one advantageous embodiment, a resistant control marker according to the invention is also resistant to the use of a composition (or formulation) comprising a substrate selected from the group consisting of luminol, isoluminol or one of their derivatives. Said composition may for example comprise hydrogen peroxide and/or chemical molecules (or cofactors) contributing to the efficacy of the luminol, isoluminol or one of their derivatives.

"Resistant to the use of a compound" or "resistant to a compound" here means that the control marker is resistant to the use of said compound during an analysis method. In particular, the control marker is resistant to being placed in the presence of said compound.

To determine whether a given compound is a resistant control marker within the meaning of the invention, it is possible to implement the method comprising the following steps:
a) depositing said compound on the surface of a solid support, to form at least one spot,
b) preferably, saturating the surface of the solid support,
c) preferably, drying the surface of the solid support,
d) optionally carrying out one or more washing steps,
e) optionally placing the spots in the presence of a detection ligand,
f) optionally carrying out one or more washing steps,
g) optionally placing the spot(s) in the presence of at least one reporter or at least one enzyme, for example a peroxidase enzyme that may or may not be coupled to a reporter,
h) optionally carrying out one or more washing steps,
i) placing the spot(s) in the presence of at least one substrate (said substrate preferably being that which will be used in the analysis method in which one wishes to implement said resistant control marker), preferably a substrate of a peroxidase enzyme, for example luminol,
j) measuring the signal produced by said compound at the spot(s), and
k) if the signal measured in step j) is a detectable signal, concluding that said compound is a resistant control marker.

The "detectable signal" is in particular as defined above.

The type of signal measured in step j) depends on the tested compound. One skilled in the art knows what type of signal must be detected and how to detect it, based on the tested compound.

The or one of the detection ligand(s) in step e) can be coupled with a detection marker of the biotin type, the or one of the reporters in step g) can be a reporter of the streptavidin type coupled to an enzyme, for example a peroxidase, and/or the or one of the substrates in step i) can be a substrate of said enzyme, for example luminol, an analogue of luminol, and/or a derivative of luminol or an analogue of luminol.

Surprisingly, the inventors have thus shown the resistant nature of control markers having simply been deposited on the surface of a solid support, mixed with a compound of interest, for example a capture ligand, in order to form spots. Thus, in one particular embodiment of the invention, a resistant control marker according to the invention is not fixed covalently to the surface of the solid support and/or is not coupled covalently to a capture ligand.

Lastly, in one preferred embodiment of the invention, a resistant control marker interferes little, or preferably not at all, with the signal produced by a detection marker of a detection ligand of an analyte used in an analysis method.

"Signal produced by the detection marker of a detection ligand of an analyte" refers to the signal produced by the detection marker of the detection ligand of an analyte itself or corresponding to the detection marker of the detection ligand. Indeed, for example, in the case of an enzyme or another type of indirect marker, the signal is not produced by the detection marker of the detection ligand of an analyte itself, but by the reporter or a compound produced by the reaction of a reporter, for example an enzyme, with its substrate; in this case, this signal corresponds to the detection marker of the detection ligand of an analyte.

The expression "a resistant control marker that interferes little with the signal produced by the detection marker of a detection ligand of an analyte" means that the functionality of the analysis method for the user is not affected by the presence of the resistant marker, in particular that the decrease in sensitivity is less than 40%, preferably less than 35%, more preferably less than 30%, still more preferably less than 25%. According to one particular embodiment, this expression furthermore means that there is no deterioration of the specificity.

The expression "there is no deterioration of the specificity" means that the increase in the threshold value is less than or equal to 40%, preferably less than or equal to 35%, more preferably less than or equal to 30%, and still more preferably less than or equal to 25%.

The threshold value is the average of the signals obtained for negative samples at the end of the analysis method plus 12 times the standard deviation of the signals of these samples.

A resistant control marker can be neutral, or positively or negatively charged.

"Positively or negatively charged molecule" means, in the present application, a molecule that includes a global charge that is respectively positive or negative, in particular that globally includes one, two, three, four or more than four respectively positive or negative charges.

A resistant control marker can comprise or be coupled to a carrier molecule, for example a protein such as BSA.

When the resistant control marker "comprises" a carrier molecule, it generally comprises or consists of a control marker (for example, a fluorophore) and a carrier molecule (for example, BSA), said control marker being coupled to said carrier molecule. This coupling can make it possible to make a control marker resistant that would not be resistant without coupling.

The coupling between a control marker or a resistant control marker and a carrier molecule results from a covalent or noncovalent bond between the resistant control marker and the carrier molecule, preferably a covalent bond.

A carrier molecule able to be coupled covalently or non-covalently to the control marker or the resistant control marker is for example selected from the group consisting of BSA, an immunoglobulin (also called Ig), a dextran, polylysine and a mixed copolymer, in particular a copolymer of different amino acids (lysine-tyrosine copolymer, for example).

Another example of a carrier molecule able to be coupled covalently or non-covalently to the control marker or the resistant control marker is an oligonucleotide or a polynucleotide, in particular a DNA or RNA.

The resistant control marker according to the invention may for example be a marker selected at the end of the selection method for a resistant control marker as defined below.

Resistant Control fluorophore

One preferred resistant control marker according to the invention is a fluorophore. In this case, it is called resistant control fluorophore.

A fluorophore, also called fluorochrome or fluorescent molecule, is a substance, in particular a chemical or protein substance (or polypeptide substance), capable of emitting fluorescent light after excitation with a light energy.

A fluorophore generally comprises several conjugated aromatic cores and/or planar and cyclic molecules that have one or several bonds π.

A fluorophore may be a fluorescent protein, for example B-Phycoerythrin.

A resistant control marker according to the invention, in particular a resistant control fluorophore, is preferably characterized in that its excitation spectrum does not overlap the emission spectrum of a detection marker of a detection ligand of an analyte or corresponding to a detection marker of a detection ligand of an analyte (used in an analysis method) and in that its emission spectrum does not overlap, or partially overlaps, the emission spectrum of a detection marker of a detection ligand of an analyte or corresponding to a detection marker of a detection ligand of an analyte (used in an analysis method).

The "emission spectrum or excitation spectrum corresponding to a detection marker of a detection ligand" is for example the emission spectrum or the excitation spectrum of a direct marker or a reporter of an indirect detection marker coupled to the detection ligand, a reporter of an indirect detection marker coupled to a reporter (in particular of an indirect detection marker of a detection ligand), or a compound produced by the reaction of an enzyme-type reporter with its substrate.

In the case of a resistant fluorophore according to the invention, the excitation spectrum may correspond to the absorption spectrum.

A preferred resistant control marker according to the invention, in particular a preferred resistant control fluorophore, is a fluorophore characterized in that its excitation spectrum does not overlap the emission spectrum of the luminol, one of its analogues, in particular the isoluminol, and/or one of their derivatives, and in that its emission spectrum does not overlap or only partially overlaps the emission spectrum of the luminol, one of its analogues, in particular isoluminol, and/or one of their derivatives.

"Emission spectrum of the luminol, one of its analogues, in particular the isoluminol, and/or one of their derivatives" refers to the emission spectrum of the chemiluminescent compound resulting from the reaction of the luminol, one of its analogues, in particular isoluminol, or one of their derivatives with a peroxidase enzyme.

Preferably, a resistant control marker according to the invention, in particular a resistant control fluorophore, is characterized in that its excitation spectrum does not overlap the emission spectrum of the luminol, the isoluminol or one of their derivatives.

When the emission spectrum of a resistant control marker according to the invention, in particular of the resistant control fluorophore, partially overlaps the emission spectrum of the detection marker of one or several detection ligands or corresponding to the detection marker of one or several detection ligands, it is advantageous to use a filter making it possible to eliminate the wavelength emitted by said detection marker to keep only the specific signal emitted by the fluorophore and/or a filter making it possible to eliminate the wavelengths emitted by said fluorophore, to keep only the specific signal emitted by said detection marker.

In one preferred embodiment, there is no energy transfer by resonance between:
the resistant control marker(s) according to the invention, in particular the resistant control fluorophore(s), and
the detection marker(s) of a detection ligand and/or the compound(s) producing a signal corresponding to the detection marker(s) of a detection ligand used in the analysis method,
in particular between the resistant control marker(s) according to the invention (in particular the resistant control fluorophore(s)) and a luminescent compound obtained by reaction of the luminol, one of its analogues, for example isoluminol, and/or one of their derivatives with a peroxidase enzyme.

In one advantageous embodiment, the resistant control marker(s) according to the invention, in particular the resistant control fluorophore(s), have excitation wavelength ranges and emission wavelength ranges that are strictly greater than the emission wavelength ranges of the luminol, one of its analogues, for example isoluminol, and/or one of their derivatives, or strictly smaller than the emission wavelength ranges of the luminol, one of its analogues, for example isoluminol, and/or one of their derivatives.

As an example, when luminol is used as substrate, a resistant control marker according to the invention, in particular a preferred resistant control fluorophore according to the invention, does not emit light around 425 nm, and in particular 375 nm to 550 nm, preferably from 375 nm to 580 nm, more preferably from 350 nm to 580 nm. In other words, when luminol is used as substrate, a preferred resistant control fluorophore according to the invention emits light outside wavelengths from 375 nm to 550 nm, from 375 nm to 580 nm or from 350 nm to 580 nm. It may for example emit light only at wavelengths less than (or less than or equal to) 375 nm, 370 nm, 360 nm or 350 nm, or only at wavelengths greater than (or greater than or equal to) 550 nm, 560 nm, 570 nm, 580 nm, 590 nm or 600 nm.

The expression "from a value X to a value Y" means that the boundaries X and Y are included.

In one particular embodiment, surprisingly, the basic pH of the reaction medium containing the luminol, an analogue of luminol and/or one of their derivatives, the presence of peroxide, one or several agents favoring electron transfers and an acylation catalyst in the reaction medium do not cause a spectral shift at the origin of a problem in the detection of the signal emitted by the receiving control marker according to the invention, and in particular by the resistant control fluorophore according to the invention.

According to one embodiment of the invention, a resistant control marker according to the invention, in particular a resistant control fluorophore according to the invention, has an absorption window that does not comprise the wavelength range corresponding to the signal emitted by the detection marker of the detection ligand and in particular that does not comprise the emission wavelength range of the luminol. For example, one preferred resistant control fluorophore according to the invention does not absorb wavelengths from 375 to 530 nm, from 375 to 550 nm, or from 350 to 580 nm (inclusive). Thus, it is for example possible to use a fluorophore that absorbs only wavelengths less than (or less than or equal to) 375, 370, 360 or 350 nm, or a fluorophore that absorbs only wavelengths greater than (or greater than or equal to) 530, 540, 550, 560, 570, 580, 590 or 600 nm.

According to one particular embodiment, a resistant control marker may be a neutral fluorophore, a positively charged fluorophore or a negatively charged fluorophore or a fluorescent protein, said fluorophore optionally being coupled to a carrier molecule, for example a protein such as BSA.

In one preferred embodiment, the resistant control fluorophore comprises at least one positively charged functional group, and in particular at least one amine function.

According to one particular embodiment, a resistant control marker comprises or consists of at least one fluorophore and at least one carrier molecule (for example, BSA), said at least one fluorophore being coupled to said at least one carrier molecule, and said at least one fluorophore for example being able to be a neutral, positively charged or negatively charged fluorophore, or a fluorescent protein.

A carrier molecule is in particular as defined above in the "analyte" paragraph.

A resistant control fluorophore is, for example, selected from the group consisting of a coumarin, a rhodamine, a carbopyronine, an oxazine, benzopyrylium, a phycoerythrin and derivatives thereof. Said fluorophore is optionally coupled to a carrier molecule, for example a protein such as BSA.

A resistant control fluorophore is, for example, selected from the group consisting of a coumarin, a rhodamine, a carbopyronine, an oxazine, a benzopyrylium derivative, their derivatives, and a phycoerythrin. A resistant control fluorophore is for example chosen from among the compounds described in application WO00/64986 A1 and/or marketed by the company Atto-Tec.

One preferred resistant control fluorophore is, for example, selected from the group consisting of a carbopyronine, an oxazine, an oxazine derivative, a benzopyrylium derivative, and a phycoerythrin.

Another preferred resistant control fluorophore is selected from the group consisting of a carbopyronine derivative, an oxazine, an oxazine derivative, a benzopyrylium derivative, and a phycoerythrin.

One still more preferred resistant control fluorophore is, for example, selected from the group consisting of a carbopyronine, a benzopyrylium derivative, and a phycoerythrin.

Another still more preferred resistant control fluorophore is, for example, selected from the group consisting of a carbopyronine derivative, a benzopyrylium derivative, and a phycoerythrin.

One example includes the Atto 633 carbopyronine marketed by the company Atto-Tec and its derivatives, in particular an amine derivative, as well as derivatives of benzopyrylium like those marketed by the company Dyomics, in particular Dye 634 or Dye 630 when they are coupled to a carrier molecule, for example BSA, or the amine derivative of Dye 634 or Dye 630, coupled or not coupled to a carrier, for example BSA.

One preferred carbopyronine according to the invention is a molecule comprising the following basic structure:

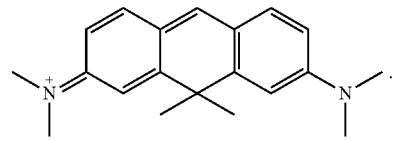

A carbopyronine able to be used as resistant control fluorophore, like the amine derivative from Atto 633, for example has the following characteristics: maximum absorption wavelength=629 nm, molar absorption coefficient at the maximum absorption wavelength=$1.3 \times 10^5$ $M^{-1}$ $cm^{-1}$, maximum emission wavelength=657 nm and quantum efficiency=64%.

A benzopyrylium derivative able to be used as resistant control fluorophore for example has the following characteristics:
maximum absorption wavelength (in ethanol): 635 nm,
maximum emission wavelength (in ethanol): 658 nm, and
molar absorption coefficient at the maximum absorption wavelength: 200,000 $M^{-1}cm^{-1}$.

This for example involves the fluorophore called Dye 634 (in its form coupled to a carrier molecule, for example BSA) with formula:

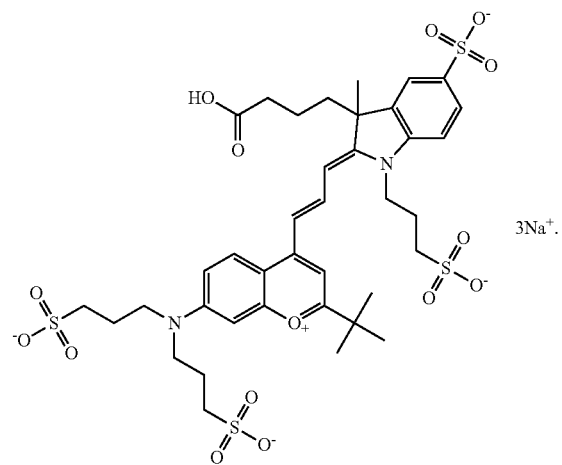

Dye 634 can also be used as resistant control fluorophore in its amine form (Dye 634-amine). It may be used coupled or not coupled to a carrier molecule, and in particular BSA Still another benzopyrylium derivative able to be used as resistant control fluorophore for example has the following characteristics:
maximum absorption wavelength (in ethanol): 636 nm,
maximum emission wavelength (in ethanol): 657 nm, and
molar absorption coefficient at the maximum absorption wavelength: 200,000 $M^{-1}cm^{-1}$.

This for example involves Dye 630 (in its form coupled to a carrier molecule, for example BSA).

Dye 630 has the following formula:

Dye 630 can also be used in its amine form (Dye 630-amine), coupled or not coupled to a carrier molecule, for example BSA.

Enzyme as Resistant Control Marker

Another example of a resistant control marker according to the invention is an enzyme for example producing a luminescent compound by reaction with a substrate of said enzyme.

Preferably, the luminescent compound is a chemiluminescent compound.

An enzyme able to be used as resistant control marker according to the invention is for example an alkaline phosphatase or a luciferase.

An alkaline phosphatase substrate is for example the Lumi-Phos 530 or Lumi-Phos substrate more marketed by Lumigen.

A luciferase substrate is for example the luciferin or coelenterazine substrate.

When the resistant control marker is an enzyme producing a luminescent compound, the detected signal corresponding to the resistant control marker is the signal emitted by the luminescent compound produced by the reaction of said enzyme with a substrate of said enzyme.

Detection of the Signal

The signal produced by the detection marker(s) of the detection ligand or produced by the resistant control marker(s) is detected directly or indirectly.

Depending on the marker used, the signal can for example be detected by fluorescence or luminescence, in particular by chemiluminescence.

The signal emitted by a marker of the fluorophore type can be read directly by fluorescence.

A marker of the enzyme type requires the addition of a substrate making it possible to produce a detectable product, for example the addition of a substrate allowing the production of light.

A resistant control marker emitting light by electroluminescence requires the addition of a Ruthenium complex and the addition of Tripropylamine (TPA), as well as the application of an electric current allowing light production.

As indicated above, an indirect marker of the biotin type requires the addition of a reporter, preferably a reporter coupled to a direct or indirect detection marker.

If the reporter is coupled to an indirect marker of the enzyme type, for example peroxidase, it is necessary to add, in a later step, the substrate of that enzyme, for example the luminol or an analogue of the luminol, such as isoluminol or a derivative of the luminol or an analogue of the luminol.

The signal may advantageously be detected using a device according to the invention, as defined below.

In another preferred embodiment, the signal emitted by the resistant control marker(s) is detected by fluorescence and the signal emitted by the detection marker(s) of the detection ligand is emitted by luminescence, for example by chemiluminescence.

Generally, the chemiluminescence reaction is done using a kit comprising at least two solutions.

The first solution comprises the substrate for the peroxidase, for example the luminol, the isoluminol and/or a derivative of the luminol or the isoluminol, and an electron mediator; the second solution comprises an oxidizer. As an example, it is possible to use the following kits: "Immun-star western C" (Bio-Rad, United States), "ELISTAR ETA C Ultra ELISA" (Cyanagen, Italy), "Supersignal West Pico" (Thermo Scientific, United States), "Chemiluminescent Sensitive Plus HRP" (Surmodics, United States).

Solid Support for Improved Detection of at Least One Analyte in a Sample

The support(s) used to carry out the analysis method according to the invention are solid supports.

According to one particular embodiment, a solid support is obtained using the method for preparing a solid support according to the invention.

A solid support can be made from any material appropriate to carry out the analysis method. A solid support is for example a support with a base of a polymer or a mixture of polymers.

An appropriate solid support is for example a support made from polystyrene, polypropylene, poly(meth)acrylate, polybutadiene or combinations thereof.

Another example of an appropriate solid support is a membrane, for example a membrane made from nitrocellulose, PVDF (polyvinylidene fluoride), nylon or combinations thereof.

Still another example of an appropriate solid support is an inorganic support, for example a glass slide and/or a metal support.

One preferred solid support is made from polystyrene or polypropylene.

A solid support comprises at least one compartment (also called analysis zone), preferably at least two compartments.

According to one particular embodiment of the invention, a solid support comprises a single compartment. Said single compartment may be a compartment including one or several walls. Alternatively, said single compartment can have no walls and then be comparable to the solid support itself. The bottom of the compartment can then consist of the upper face of the solid support. One example of such a solid support comprising a single compartment that may or may not include one or several walls is a slide or a membrane.

According to one particular embodiment of the invention, the solid support, which may for example be a microplate or a membrane, comprises at least two compartments.

When the solid support comprises at least two compartments, they are isolated from one another, such that they do not communicate with one another, i.e., such that the various compositions or solutions used for the analysis cannot circulate from one compartment to another during the analysis. Thus, a solution added into one compartment will not go into the other compartments. For example, the compartment(s) comprise or are made up of a bottom and one or several walls, said wall(s) isolating the compartment(s) from one another such that they do not communicate with one another.

Typically, at least one (for example one or two) compartment of the solid support is used per sample to be analyzed.

In one particular embodiment of the invention where the solid support (for example a slide or a membrane) comprises a single compartment, typically, at least one (for example one or two) solid support is used per sample to be analyzed.

The solid support is for example a microplate. In this case, one example compartment is a well.

A microplate is typically a microplate with 96 wells or 384 wells.

The present invention thus relates to a solid support for detecting at least one analyte in at least one sample, characterized in that said solid support comprises at least one compartment comprising at least one spot, said spot comprising at least one resistant control marker and at least one capture ligand.

A resistant control marker is in particular as defined above, in particular in the paragraph "resistant control marker", "resistant control fluorophore" and "enzyme as resistant control marker", or as obtained using the selection method defined below in the paragraph "selection method of a resistant control marker".

In particular, said resistant control marker(s) are markers that remain at least partially fixed at said spot on the surface of the solid support during the implementation of a method for detecting at least one analyte, so as to produce a detectable signal at the end of the detection method.

A compartment of the solid support intended to analyze a sample comprises at least one spot, for example two spots, three spots, four spots or five spots, or at least six spots, preferably six spots, seven spots, eight spots, more preferably at least nine spots, for example nine spots, ten spots, eleven spots, twelve spots, thirteen spots, fourteen spots, fifteen spots, sixteen spots or more than sixteen spots.

"Spot" here refers to a zone on the surface of a compartment of a solid support comprising at least one resistant control marker and/or at least one compound of interest, preferably at least one resistant control marker and at least one compound of interest, for example a capture ligand. The resistant control marker(s) and the compound(s) of interest thus fix at the same time to said zone on the surface of the compartment, through noncovalent physicochemical interactions (in particular of the weak bond type, for example, ionic, van der Waals, hydrogen and/or hydrophobic) and/or by covalent bonds.

A spot may comprise, aside from the compound(s) of interest, at least one polymer, in particular at least one polymer including hydrophilic groups, for example at least one hydrogel.

In one particular embodiment, all of the spots of a compartment, preferably all of the spots of a solid support, comprise a single resistant control marker or a single mixture of resistant control markers that may be used at a same concentration in all of the spots or at different concentrations.

Alternatively, different (at least two) resistant control markers and/or different (at least two) mixtures of resistant control markers can be used in spots of a same compartment of a solid support.

The present invention particularly relates to a solid support for detecting at least one analyte in at least one sample, characterized in that said solid support comprises at least one compartment comprising at least one spot, said spot comprising a single resistant control marker and at least one capture ligand.

Preferably, all of the spots intended to detect an analyte, in particular all of the spots comprising a capture ligand, comprise only one resistant control marker, which is preferably the same in all of the spots intended to detect an analyte of a same compartment, and more preferably, which is the same in all of the spots intended to detect an analyte of all of the compartments of a solid support.

A spot corresponds to a well-defined zone, for example comprised between 0.0078 mm$^2$ to 5.309 mm$^2$, preferably from 0.196 mm$^2$ to 3.142 mm$^2$, more preferably comprised from 0.503 mm$^2$ to 2.011 mm$^2$.

A spot may have a discoid, cylindrical or hemispherical shape, or approximately discoid, cylindrical or hemispherical shape, for example oval, in particular when the solid support is a microplate or a slide.

Alternatively, a spot may have a square or rectangular shape (in particular a strip), for example when the solid support is a membrane, or any other shape.

The spots are obtained using techniques well known by those skilled in the art, such as those disclosed in patents U.S. Pat. No. 7,470,547 B2, U.S. Pat. No. 6,576,295 B2, U.S. Pat. No. 5,916,524 A and U.S. Pat. No. 5,743,960 A.

For example, a spot is obtained by depositing at least one drop of a solution containing a determined quantity of at least one resistant control marker and at least one compound of interest in a specific location on the surface of the compartment of the solid support.

When a spot comprises at least one polymer (for example at least one hydrogel), said spot may be obtained by depositing at least one drop of a solution containing a determined quantity of at least one resistant control marker and at least one compound of interest in a specific location on the surface of the compartment on which said polymer has been previously deposited.

The surface of a compartment is also called "solid phase".

A compound of interest is generally a capture ligand, in particular a capture ligand of an analyte. One or several spots of a compartment can serve as control spot and thus comprise a capture ligand that is not intended to detect an analyte of the sample, or comprise another compound of interest, or not comprise any compound of interest.

The present invention particularly relates to a solid support for detecting at least one analyte in a sample, characterized in that said solid support comprises at least two compartments comprising at least one spot, said spot comprising at least one resistant control marker and at least one capture ligand.

In one particular embodiment, some or all of the compartments of a solid support have the same spot composition.

In another particular embodiment, some or all of a solid support or compartments of a solid support comprises or consists of several (for example two) distinct groups (or types) of spots or compartments, each of the separate groups having a different spot composition (due to the number of spots and/or the resistant control marker(s) and/or the capture ligand(s) and/or the compound(s) of interest present in the spots of each group).

Preparation of an Analysis Support Comprising a Resistant Control Marker

The present invention also relates to a method for preparing a solid support for detecting at least one analyte in at least one sample comprising the following steps:

a) depositing, on the surface of at least one compartment, preferably at least two compartments, of a solid support, a mixture comprising at least one resistant control marker and at least one capture ligand, to obtain a spot, b) repeating step a) n−1 times, n being an integer greater than or equal to 1, to obtain n spots intended to detect an analyte on the surface of said compartment(s), c) optionally, saturating the surface of said compartment(s), and d) optionally, drying the surface of said compartment(s).

The solid support, the resistant control marker(s) and the capture ligand(s) are in particular as defined above.

In step a), a mixture comprising at least one resistant control marker and at least one capture ligand is deposited on the surface of at least one compartment of a solid support, preferably at least two compartments of a solid support, to obtain a spot.

In step a), said resistant control marker(s) are markers that remain at least partially fixed at said spot on the surface of the solid support during the implementation of a method for detecting at least one analyte, so as to produce a detectable signal at the end of the detection method.

A resistant control marker is in particular as defined in the present application.

Said resistant control marker(s) are preferably fluorophores, for example a mixture of fluorophores. The fluorophore(s) can be fluorescent chemical molecules or fluorescent proteins.

Said capture ligand(s) are preferably selected from the group consisting of an antibody, an antigen, a nucleic acid and combinations thereof.

In another preferred embodiment, said capture ligand(s) are not nucleic acids.

For example, said capture ligand(s) are selected from the group consisting of an antibody and an antigen.

The mixture is preferably a solution.

A resistant control marker is present in the mixture at a concentration that does not interfere with the fixing of the capture ligand(s) to the surface of the compartment and allows detection of the signal produced by said resistant control marker at the end of the analysis method.

As an example, the mixture comprises 0.1 to 100 µg/ml of a capture ligand and 0.01 to 100 µg/ml of a control marker, preferably in a buffer solution, for example a TBS (Tris Buffered Saline) solution.

The concentration of a resistant control marker in the mixture can for example be determined using the method comprising the following steps:

depositing at least two solutions on the surface of a solid support, each solution comprising said resistant control marker and a capture ligand, the concentration of the resistant control marker increasing from one solution to the other and the lowest concentration of the resistant control marker being greater than or equal to a predefined minimum concentration, optionally, saturating the surface of the solid support, i.e., placing the surface of the solid support in the presence of an agent making it possible to avoid nonspecific bonds to the solid support, optionally, drying the surface of the solid support, placing a sample including an analyte having a specific capture ligand in the presence of spots, placing a specific detection ligand of said analyte in the presence of spots, said detection ligand being coupled to a direct or indirect detection marker, when said detection ligand is coupled to an indirect detection marker, adding a reporter (also called first reporter) of said indirect detection marker and when said (first) reporter is coupled to an indirect detection marker, adding a second reporter of the indirect detection marker coupled to said (first) reporter of the indirect detection method of the detection ligand, detecting a signal produced by the resistant control marker, detecting a signal produced by the detection marker of the detection ligand, and selecting a concentration of resistant control marker that makes it possible to detect both the signal produced by the resistant control marker and the signal produced by the detection marker of the detection ligand.

The concentration of resistant control marker preferably makes it possible to detect both the signal produced by the resistant control marker and the signal produced by the detection marker of the detection ligand, without significant loss of sensitivity relative to a spot not comprising the resistant control marker, i.e., the functionality of the analysis method for the user is not affected by the presence of the resistant marker, in particular that the decrease in sensitivity is less than 40%, preferably less than 35%, more preferably less than 30%, still more preferably less than 25%.

According to one particular embodiment, the concentration of resistant control marker makes it possible to detect both the signal produced by the resistant control marker and the signal produced by the detection marker of the detection ligand without deterioration of the specificity.

The expression "there is no deterioration of the specificity" means that the increase in the threshold value is less than or equal to 40%, preferably less than or equal to 35%, more preferably less than or equal to 30%, and still more preferably less than or equal to 25%.

The threshold value is the average of the signals obtained for negative samples at the end of the analysis method plus 12 times the standard deviation of the signals of these samples.

When a detection ligand is coupled to an indirect detection marker, a reporter of said indirect detection marker is therefore added. When said reporter (called first reporter) is itself is coupled to an indirect detection marker, for example an enzyme, a second reporter, for example a substrate, of the indirect detection marker coupled to said first reporter is added.

The predefined minimum concentration of resistant control marker can for example be determined using the following method:

depositing at least two solutions on the surface of a solid support, each solution comprising a resistant control marker and not comprising capture ligand, the concentration of the resistant control marker increasing from one solution to the other, to form at least two spots, optionally, saturating the surface of the solid support, i.e., placing the surface of the solid support in the presence of an agent making it possible to avoid nonspecific bonds to the solid support, optionally, drying the surface of the solid support, optionally carrying out at least one of the following steps:
  (i) performing one or more washing steps,
  (ii) placing the spot(s) in the presence of a detection ligand,
  (iii) placing the spot(s) in the presence of a reporter,
  (iv) placing the spot(s) in the presence of a substrate, detecting the signal produced by the resistant control marker, and selecting the minimum concentration of resistant control marker that allows the detection of a signal.

The mixture (or solution) can be deposited on the surface of the solid support or a compartment of the solid support manually, but preferably is done automatically by an appropriate device.

Thus, as previously indicated, a resistant control marker fixes on the solid phase of the analysis support at the same time as the capture ligand(s) present in the mixture (or solution).

In one particular embodiment of the invention, each spot of a compartment of the solid support intended to detect at least one analyte comprises at least one different capture ligand, preferably intended to detect an analyte by spot. However, several spots of a compartment may comprise at least one same capture ligand.

In one particular embodiment of the invention, a same spot may comprise several different capture ligands (for example, several antibodies and/or antigens), which are generally specific to a same pathology, infection or disease to be detected (in particular specific to a same virus, a same bacteria, a same fungus or a same parasite), the evolution of an infection or disease, a condition (pathological or not) of the subject, a risk of developing a condition (pathological or not) or a marker of resistance to a treatment.

Several spots or all of the spots of a compartment may comprise capture ligands intended to detect a same analyte; this for example involves different specific capture ligands of a same analyte or even a same capture ligand present at different concentrations in the spots.

In one particular embodiment, the resistant control marker or the mixture of resistant control markers is the same in all of the spots, and it may or may not be added at a same concentration in each spot.

Alternatively, different resistant control markers (at least two) and/or different mixtures of resistant control markers can be used in different spots of a compartment.

A compartment may also comprise one or several spots with no resistant control marker. However, preferably, all of the spots of said compartment comprise a resistant control marker.

A compartment may also comprise one or several spots with no capture ligand, but preferably comprising another compound of interest.

When a compartment comprises one or several spots with no capture ligand, the spot(s) preferably comprise a resistant control marker.

In one particular embodiment of the invention, all of the compartments of the support have the same spot composition.

In another particular embodiment of the invention, some or all of the compartments of a solid support comprise or consist of several (for example two) distinct groups of compartments, each of the distinct groups having a different spot composition.

Steps a) and b) are carried out in some or all of the compartments of the solid support, preferably, in all of the compartments of the solid support.

The mixture deposited on the surface of at least one compartment of the solid support is incubated for example from several seconds to several hours, for example at a temperature comprised from 4° C. to 40° C.

The method comprises a potential step c) for saturating the surface of said compartment(s) of the solid support, i.e., testing of placing the surface of the solid support in the presence of an agent making it possible to avoid nonspecific bonds to the solid support. The saturation step is in particular intended to prevent the nonspecific fixing of compounds, during the implementation of the analysis method.

The agent making it possible to avoid nonspecific bonds to the solid support is for example a saturation solution well known by those skilled in the art.

In the potential step d), the surface of the compartment(s) is dried.

The drying is for example done at 56° C. or 37° C. or at ambient temperature.

In one particular embodiment, step a), step b) and/or step c) are followed by one or several washing steps.

The present invention also relates to a method for preparing a solid support as defined above, comprising a subsequent step e) consisting of checking the quality of the spots.

If the quality check of a spot is positive, said spot can be used as part of an analysis method.

If the quality check of a spot is negative, said spot cannot be used as part of an analysis method, potentially as well as the compartment containing said spot.

The present invention also relates to a kit, characterized in that it comprises or consists of at least one solid support according to the invention or obtained using the preparation method according to the invention and, if applicable, at least one composition or solution to be used to carry out an analysis method according to the invention and/or user instructions.

Device for Improved Detection (or Device for Double Detection)

The present invention also aims to provide a device for detecting at least one analyte in a sample, said device comprising:
 means for detecting a first signal and a second signal produced at a solid support, and
 means for defining a reading grid from the location of said first signal and for reading said second signal at said reading grid.

According to one particular embodiment, this reading corresponds to a quantification of the second signal at the regions of interest.

The detection of the first signal can be done before, after or simultaneously with the detection of the second signal.

The solid support is in particular as defined above.

The first signal can be a fluorescence or luminescence signal, for example by chemiluminescence.

The second signal can be a fluorescence or luminescence signal, for example by chemiluminescence.

In one preferred embodiment, the first signal is a fluorescence signal and the second signal is a luminescence signal, preferably by chemiluminescence (or vice versa).

The means for detecting a first signal and a second signal produced at a solid support are called optical bench.

An optical bench may for example comprise or be made up of:
 a lighting system,
 a telecentric objective,
 a filter wheel, said telecentric objective preferably being coupled on its output lens to said filter wheel, and
 a camera.

The lighting system is preferably a steerable lighting system.

The lighting system makes it possible to illuminate the solid support more or less intensity with, for example to reveal the fluorescence or the geometry of the solid support used.

The telecentric objective is preferably large. In particular, the telecentric objective covers the entire solid support.

The telecentric objective makes it possible to image the entire surface to be measured without deforming the image, to eliminate the parallax error inherent to standard objectives and to guarantee signal homogeneity over the entire viewed surface.

The telecentric objective is preferably coupled on its output lens to a filter wheel.

The filter wheel makes it possible to present different filters between the telecentric objective and the camera (also called image acquisition camera). In one preferred embodiment, it is thus possible to select the wavelengths reaching the sensor of the camera to be able, in one case, to separate the excitation signals of the lighting from those emitted by at least one resistant control marker (in particular at least one fluorophore) through the presence of a filter, and, in the other case, to collect the maximum amount of signal produced by at least one detection marker of a detection ligand of an analyte through the presence of a neutral window not filtering the signal but guaranteeing the maintenance of the optical properties of the assembly.

The camera makes it possible to acquire an image with variable exposure times.

The optical bench thus defined makes it possible to take a series of images of the same support, with different lighting, filtering and/or image acquisition parameters, such as:
- an image in the visible domain (also called positioning image), for example by using the lighting from the lighting system, but no specific filter,
- a fluorescence image (also called detection image), by using the lighting from the lighting system and a specific filter for the sought fluorescence,
- an image with no lighting and no specific filter (also called analysis image), for example to reveal a chemiluminescence signal.

The means for defining a reading grid from the location of said first signal and for reading the second signal at said reading grid can comprise or be made up of an imaging system.

In one advantageous embodiment, the optical bench is therefore associated with an imaging system making it possible to carry out an analysis method comprising several steps that in particular guarantee the accuracy and robustness of the analysis performed, said steps comprising:
1. searching for and positioning the solid support and the compartment(s) of the solid support, in particular owing to the positioning image; the purpose of this processing is to reduce any mechanical positioning errors of the solid support and make it possible to use mechanics not having a high positioning precision;
2. from the position of the compartment(s) determined in step 1, positioning, in each compartment, a theoretical grid representing the theoretical position of each of the spots; this positioning can be done from a reference grid, for example described in the analysis system, said reference grid indicating the coordinates of each of the spots relative to a reference point of the compartment; the reference point of the compartment is for example the center of the compartment;
3. searching, using the detection image done with the lighting and the fluorescence filter, for all of the fluorescent events existing in the compartment(s) of the solid support, and optionally, rejecting certain events using a selection of events by their size and shape so as to eliminate those that are completely outside the expected specifications;
4. comparison between:
    the position of the events previously detected and considered valid,
    the theoretical position of the expected spots as defined in step 2;
5. for each of the expected spots, association with the closest detected event and intersecting the surface of the theoretical spot so as to form "theoretical spot"/"fluorescent event" pairs making it possible to detect the missing spots. For each theoretical spot, a distinct and unique fluorescent event must exist;
6. characterization of each of the detected spots using diameter, shape, distance from the theoretical position criteria making it possible to guarantee the integrity of the detected spots;
7. for each of the detected spots, definition of the corresponding region of interest, called reading grid, in particular defined by the surface and coordinates of the detected spots; and
8. reading of the second signal on the reading grid defined in step 7, in particular quantification of the second signal on the analysis image at this region of interest, i.e., the reading grid.

Analysis Method with Quality Check of the Spots

The analysis method according to the invention allows the detection of at least one analyte in at least one sample.

The present invention in particular relates to a method for detecting at least one analyte in at least one sample comprising the following steps:
a) placing a sample to be analyzed in the presence of the spot(s) of the compartment of a solid support, said spot or at least one of said spots comprising at least one resistant control marker and at least one capture ligand of an analyte,
b) placing at least one detection ligand of an analyte in the presence of the spot(s) of said compartment, said detection ligand of an analyte being coupled to a direct or indirect detection marker,
c) when at least one detection ligand of an analyte is coupled to an indirect detection marker, placing a reporter of said indirect detection marker in the presence of the spot(s) of said compartment,
d) when the reporter used in step c) is coupled to an indirect detection marker, placing a reporter of the indirect detection marker coupled to said reporter used in step c) in the presence of the spot(s) of said compartment,
e) detecting a signal produced by at least one resistant control marker in said compartment,
f) defining a reading grid from the location of the signal detected in step e),
g) optionally, detecting a signal produced by at least one detection marker of a detection ligand of an analyte, and
h) optionally, reading the signal detected in step g) on the reading grid defined in step f).

As defined above, the or said resistant control markers are capable of producing a detectable signal at the end of an analysis method, i.e., to produce a detectable signal at a spot when the analysis method has taken place without deterioration of said spot. In particular, the or said resistant control markers are capable of producing a detectable signal during step e) of the method above.

The present invention in particular relates to a method for detecting at least one analyte in at least one sample comprising the following steps:
a) placing a sample to be analyzed in the presence of the spot(s) of the compartment of a solid support, said spot or at least one of said spots comprising at least one resistant control marker and at least one capture ligand of an analyte, b) placing at least one detection ligand of an analyte in the presence of the spot(s) of said compartment, said detection ligand of an analyte being coupled to a direct or indirect detection marker, c) when at least one detection ligand of an analyte is coupled to an indirect detection marker, placing a reporter of said indirect detection marker in the presence of the spot(s) of said compartment, d) when the reporter used in step c) is coupled to an indirect detection marker, placing a reporter of the indirect detection marker coupled to said reporter used in step c) in the presence of the spot(s) of said compartment, e) detecting a signal produced by at least one resistant control marker in said compartment, f) defining a reading grid from the location of the signal detected in step e), g) optionally, detecting a signal produced by at least one detection marker of a detection ligand of an analyte, and h) optionally, reading the signal detected in step g) on the reading grid defined in step f), said resistant control marker(s) being markers that remain at least partially fixed at the spot on the surface of the solid support during the implementation of said method for detecting at least one analyte, so as to produce a detectable signal during step e).

Steps a) to d) are still done before steps e) to h).

Step g) can be carried out before, after or at the same time as step e). In one particular embodiment, step g) is carried out before or after step e).

Step f) is still carried out after step e).

Step f) is still carried out after step e) and before step h), and can be carried out before, after or at the same time as step g).

Step h) is still carried out after steps e) to g).

Steps a) to f) and, if applicable, step g) and/or step h) are done for each compartment of a solid support comprising at least one spot comprising at least one resistant control marker and at least one capture ligand of an analyte, in which a sample is analyzed.

Steps g) and/or h) may not be done if the reading grid defined in step f) does not indicate any zone for reading the signal to be detected in step g).

If step h) is carried out, step g) is also carried out.

The method may advantageously comprise one or several washing steps, for example between each or some of steps a) to d).

The washing of each compartment intended to analyze a sample comprises at least one cycle, preferably 3 to 6 cycles, for distributing and aspirating a volume (for example 400 μL) of a washing solution (for example, a Tris NaCl 0.01 M buffer solution, pH 7.4, doped with Tween 20 at 0.1%).

According to one particular embodiment of the invention, no operation and in particular no pipetting, distributing, agitating, aspirating or washing step is done between steps e) and g), irrespective of the order in which steps e), f) and g) are carried out.

The expression "place a compound X in the presence of the spots of a compartment" means that the compound X is added into a compartment comprising said spots, said compartment being intended to analyze a sample.

When at least two compounds are to be placed in the presence of the spot(s) of the compartment during a same step and/or when at least two steps a) to d) are done at the same time, said compounds may be placed in the presence of said spot(s) separately, i.e., contributed in the form of separate compositions; alternatively, said compounds or some of the compounds may be placed in the presence of the spot(s) of a compartment in the form of one or several mixtures.

The detection method is in particular carried out using a solid support as defined above or obtained by the preparation method as defined above.

The resistant control marker(s), the spot(s), the capture ligand(s) of an analyte are in particular as defined above.

In particular, the resistant control marker(s) are markers that remain at least partially fixed at said spot on the surface of the solid support during the implementation of said method for detecting at least one analyte, so as to produce a detectable signal during step e), i.e., when the analysis method has taken place without deterioration of a spot.

The present invention particularly relates to a method as defined above, characterized in that said or one of said resistant control markers is (are) one (or several) fluorophore(s), for example one or several fluorescent chemical molecules or one or several fluorescent proteins, for example a mixture of fluorophores.

The present invention particularly relates to a method as defined above, characterized in that said or one of said resistant control markers is a resistant control marker, in particular a fluorophore, whereof the excitation spectrum does not overlap the emission spectrum of the signal emitted by or corresponding to the detection marker of said detection ligand(s) of an analyte and whereof the emission spectrum does not overlap, or partially overlaps, the emission spectrum of or corresponding to the detection marker of said detection ligand(s) of an analyte.

The present invention for example relates to a method as defined above, characterized in that said or one of said resistant control markers is a resistant control marker, in particular a fluorophore, whereof the excitation spectrum does not overlap the emission spectrum of the signal emitted by a luminescent compound obtained by reaction of the luminol and/or an analog and/or a derivative of the luminol or an analogue of the luminol with a peroxidase enzyme and whereof the emission spectrum does not overlap, or partially overlaps, the emission spectrum of a luminescent compound obtained by reaction of the luminol and/or an analogue and/or a derivative of the luminol or an analogue of the luminol with a peroxidase enzyme.

In one preferred embodiment, the detection method as defined above comprises the following steps:

a) placing a sample to be analyzed in the presence of the spot(s) of the compartment of a solid support, said spot or at least one of said spots comprising at least one resistant control marker and at least one capture ligand of an analyte, b) placing at least one detection ligand of an analyte in the presence of the spot(s) of said compartment, said detection ligand of an analyte being coupled to an indirect detection marker, c) placing a reporter of said indirect detection marker in the presence of the spot(s) of said compartment, d) when the reporter used in step c) is coupled to an indirect detection marker, placing a reporter of the indirect detection marker coupled to said reporter used in step c) in the presence of the spot(s) of said compartment, e) detecting a signal produced by at least one resistant control marker in said compartment, f) defining a reading grid from the location of the signal detected in step e), g) optionally, detecting a signal produced by at least one detection marker of a detection ligand of an analyte, and h) optionally, reading the signal detected in step g) on the reading grid defined in step f).

The present invention particularly relates to a method as defined above, characterized in that:

the signal produced by at least one detection marker of a detection ligand of an analyte is the light emitted by a chemiluminescent compound obtained by reaction of a peroxidase with the luminol, an analogue of the luminol and/or a derivative of the luminol or an analogue of the luminol, and the signal produced by the or said resistant control marker(s) is a light emitted outside the wavelengths from 375 to 550 nm, from 375 to 580 nm, or from 350 to 580 nm (inclusive).

Preferably, the resistant control marker(s) have an excitation spectrum and, preferably, an emission spectrum outside the wavelengths from 375 to 550 nm, from 375 to 580 nm, or from 350 to 580 nm (inclusive).

The analysis method is for example an immunoassay, and in particular an immuno-enzymatic assay, such as an ELISA (Enzyme-Linked ImmunoSorbent Assay) test. The analysis method can also be used to detect nucleic acids.

In step a), a sample to be analyzed is placed in the presence of the spot(s) of a compartment of the solid support.

When several samples are analyzed and the solid support comprises several compartments, step a) comprises placing a sample in the presence of the spot(s) of at least one compartment of a solid support, said solid support comprising at least as many compartments comprising at least one spot comprising at least one resistant control marker and at least one capture ligand of an analyte as the number of samples to be analyzed or several solid supports are used.

When several samples are analyzed and the solid support comprises a single compartment, step a) comprises adding a sample into the compartment of a solid support (or, when said compartment is comparable to the solid support itself, adding a sample on said solid support), and one uses at least as many solid supports comprising a compartment comprising at least one spot comprising at least one resistant control marker and at least one capture ligand of an analyte as the number of samples to be analyzed.

When several samples are analyzed, a different compartment is used for each sample. It is also possible to use several compartments of one or several solid supports to analyze a same sample, in particular if said compartments have a different spot composition.

Steps a) and b) can be done at the same time, step a) before step b), or step b) before step a). When step b) is done before step a), the method does not comprise a washing step between these two steps a) and b).

When they are present, steps c) and d) are preferably done after steps a) and b) and there is preferably at least one washing step between steps a) and b) and steps c) and d).

When they are present, steps c) and d) can be done at the same time, or step c) before step d). When step d) is done before step c), the method does not comprise a washing step between these two steps d) and c).

When it is present, step d) is preferably done after step c) and there is at least one washing step between steps c) and d).

In step b), at least one detection ligand of an analyte is placed in the presence of the spot(s) of said compartment.

Step b) is in particular done in each compartment intended to analyze a sample.

The detection ligand(s) of an analyte are in particular as defined above.

Preferably, step b) comprises adding at least one detection ligand of each analyte to be detected. When different detection ligands of an analyte are used, they may be added at the same time or one after the other, all or part of the ligands being able to be contributed in the form of separate compositions or of one or several mixtures. Some of the detection ligands of an analyte may be added simultaneously with step a), preferably followed by a washing step before adding the rest of the detection ligands of an analyte.

When detection ligands of an analyte are added successively during step b), each addition of at least one analyte detection ligand can be followed by a washing step of the compartment intended to analyze a sample.

The performance of steps c) and d) depends on the detection marker of the detection ligand and, if applicable, the detection marker of the reporter of the detection marker of the detection ligand.

Thus, step c) is carried out when at least one detection ligand of an analyte is coupled to an indirect detection marker.

Preferably, the detection ligand(s) of an analyte are coupled to the same detection marker. If at least two detection ligands of an analyte are coupled to different indirect detection markers, step c) is carried out for each indirect detection marker, in order to detect the signal of each marker.

Step d) is carried out when at least one reporter (also called first reporter) used in step c) is coupled to an indirect detection marker. The reporter used in step d) is called second reporter.

When step d) is carried out, step c) is therefore also carried out.

In step e), a signal produced by at least one resistant control marker is detected in said compartment.

If at least two resistant control markers are used, step e) preferably comprises detecting a signal produced by each of said resistant control markers.

The detection of the signal produced by at least one resistant control marker in particular makes it possible to localize each spot comprising at least one resistant control marker in each compartment of the solid support.

The signal produced by at least one resistant control marker is preferably a signal emitted by fluorescence.

In step f), a reading grid is defined from the location of the signal detected in step e).

The reading grid indicates precisely in which zone(s) of the compartment the second signal must be read (or "analyzed" or "taken into account" or "interpreted"). In particular, a second signal detected in step g) outside the or one of the zones defined in the reading grid is not taken into account in the reading (or the "analysis" or the "interpretation") of the second signal during step h).

It is particularly advantageous to define said zones precisely according to the contour of each spot.

Step f) for defining the reading grid therefore in particular comprises verifying the quality of the spots, from the signal detected in step e), which corresponds to at least one resistant control marker.

"Quality of the spots" refers to the presence, location and/or integrity of the spot(s).

The integrity of the spots comprises the size and shape of the spot.

A quality check of a spot is in particular positive if the spot is present in the compartment in a position in line with the expected position, if it has a well-defined contour, if its shape is in line with the acceptability criteria, for example, if it has a discoid, approximately discoid, for example oval shape or a shape with a circularity greater than 80%, and if it does not intersect another spot of the compartment.

A "circularity greater than 80%" means that the detected spot has a sufficient circularity to guarantee that it has not been damaged by all of the treatments done during the analysis method.

For example, a quality check of a spot is positive if a signal is detected in step e), this signal has a well-defined contour, a discoid shape, an approximately discoid shape, for example oval or a with a circularity greater than 80%, and if it does not intersect the signal produced by another spot of the compartment.

If no signal is detected in step e) at a spot or if the spot does not meet the quality control for at least one other of the reasons indicated above, the second signal optionally detected in step g) at said spot is not taken into consideration when reading the second signal in step h), potentially as well as the second signal detected at each spot of the compartment corresponding to said spot.

In steps e) and g), the detection of a signal preferably comprises the acquisition of a signal.

The use of one or several resistant control marker(s) according to the invention thus makes it possible to perform a reading of the second signal in the precise locations where the spots are located, making it possible to improve the sensitivity of the analysis, while securing the rendered results, in particular by making it possible to eliminate false positives or false negatives related to a spot flaw.

The present invention particularly relates to the method as defined above, characterized in that the signal produced by at least one detection marker of a detection ligand of an analyte is a luminescent signal, in particular a chemiluminescent signal, for example the light emitted by reaction of the luminol and/or an analogue and/or a derivative of the luminol or of an analogue of the luminol with a peroxidase enzyme.

The present invention more particularly relates to a method as defined above, characterized in that the signal produced by at least one resistant control marker is detected by fluorescence and the signal produced by at least one detection marker of a detection ligand of an analyte is detected by luminescence, in particular chemiluminescence.

In one preferred embodiment, at least steps e) to h) are carried out using a same device, for example the device as described in the "device for improved detection" section.

In another preferred embodiment, all of the steps of the method are carried out using a same device, for example the device as described in the "device for improved detection" section.

Method for Selecting a Resistant Control Marker

The present invention also relates to a method for selecting a resistant control marker, comprising the following steps:
a) depositing a marker to be tested on the surface of a solid support, to form at least one spot,
b) optionally, saturating the surface of the solid support,
c) optionally, drying the surface of the solid support,
d) carrying out at least one of the following steps:
   (i) performing one or more washing steps,
   (ii) placing the spot(s) in the presence of a detection ligand,
   (iii) placing the spot(s) in the presence of a reporter,
   (iv) placing the spot(s) in the presence of a substrate,
e) selecting a marker that produces a signal at the end of step d).

The marker to be tested is a compound that produces (for example, emits) a signal able to be detected. For example, the marker to be tested is a fluorophore or a luminescent compound.

The solid support is in particular as defined above.

Step a) comprises or consists of depositing a marker to be tested on the surface of a solid support, to form at least one spot.

The marker can be deposited manually or automatically using an appropriate device.

The marker to be tested is generally deposited in the form of a solution comprising said marker.

Step a) can comprise depositing a same marker to be tested in several spots, and increasing concentrations.

The solution deposited in step a) may or may not comprise a capture ligand.

The method comprises a potential step b) for saturating the surface of the solid support. The saturation step is in particular intended to prevent the nonspecific fixing of compounds, during the implementation of the analysis method.

In step c), the surface of the solid support is optionally dried.

Generally, step a) and/or step b) are followed by one or several washing steps a') and/or b').

Step d) comprises or consists of carrying out at least one of the following steps, preferably at least two of the following steps, more preferably at least three of the following steps:
(i) performing one or more washing steps,
(ii) placing the spot(s) in the presence of at least one detection ligand,
(iii) placing the spot(s) in the presence of at least one reporter, and/or
(iv) placing the spot(s) in the presence of at least one substrate.

In one preferred embodiment, step d) comprises or consists of step (iii) and/or step (iv), preferably step (iii) and step (iv).

In another preferred embodiment, step d) comprises or consists of step (i), step (iii) and/or step (iv), preferably step (i), step (iii) and step (iv).

In one preferred embodiment, step d) comprises at least step (i), step (ii), step (iii) and step (iv).

Steps (i) to (iv) can be done in any desired order.

However, in one preferred embodiment, step d) comprises the following steps and in the following order: step (ii), step (i), step (iii), step (i), step (iv) and step (i).

In another preferred embodiment, step d) comprises the following steps and in the following order: step (ii), step (i), step (iii), step (i) and step (iv).

In another preferred embodiment, when these steps are present, step (ii) is carried out before step (iii) and/or before step (iv) and step (iii) is carried out before step (iv). Step (i) can be carried out between steps (ii) and (iii), (ii) and (iv) (in particular when step (iii) is absent) and/or (iii) and (iv).

Preferably, the or one of the reporters of step (iii) is the reporter of a detection marker coupled to at least one detection ligand of step (ii) and/or the or one of the substrates of step (iv) is a reporter of a detection marker coupled to a reporter.

For example, the or one of the detection ligand(s) of step (ii) is coupled with a detection marker of the biotin type, the or one of the reporters of step (iii) is a reporter of the streptavidin type coupled to an enzyme, for example a peroxidase, and/or the or one of the substrates in step (iv) is a substrate of said enzyme, for example luminol, an analogue of luminol, and/or a derivative of luminol or an analogue of luminol.

The selection method comprises a step e) for selecting a marker that produces a signal at the end of step d). In particular, the marker selected in step e) produces a signal at the end of step d). A "detectable signal" is in particular as defined above.

Preferably, step e) further comprises selecting a marker that does not interfere or interferes little with the detection of the signal produced by a detection marker of a detection ligand.

The selection method according to the invention may also comprise:
optionally, first:
steps a) to c) above, in which the spot(s) formed in step a) do not comprise a capture ligand,
optionally, a first preselection step comprising selecting a marker that produces a detectable signal at the end of step c),
optionally, steps d) to e) on the same support, preferably said steps only being carried out with said marker selected in the first preselection step, followed by a second preselection step comprising selecting a marker that produces a detectable signal at the end of step c),
secondly, steps a) to e) above, in which the spot(s) formed in step a) comprises a capture ligand, steps d) to e) preferably being done only with a marker selected in said first preselection step and/or selected in said second preselection step.

Use of a Resistant Control Marker

The present invention also relates to the use of at least one resistant control marker in at least one spot intended to detect an analyte to secure a method for detecting at least one analyte in a sample or at least one sample.

"To secure a method for detecting at least one analyte in a sample or at least one sample" here means guaranteeing the reliability of the results obtained at the end of said detection method, in particular by avoiding the presence of "false negatives" or "false positives".

A "false negative" is a negative result reflecting the absence of one or several analytes to be detected in a sample, whereas said analyte(s) were present in the sample and should have been detected.

A "false positive" is a positive result reflecting the presence of one or several analytes to be detected in a sample, whereas said analyte(s) were absent from the sample.

The securing of the method for detecting at least one analyte in a sample is in particular obtained by checking, at the end of the detection method, the quality of the spot(s) intended to detect an analyte and/or by improving the sensitivity of the detection of the analytes, through the use of at least one resistant control marker.

The present invention thus relates to the use of at least one resistant control marker in at least one spot intended to detect an analyte to secure a method for detecting at least one analyte in a sample or at least one sample, characterized in that it comprises:
checking the quality of said spot, after said spot has been placed in the presence of the sample and at least one detection ligand of an analyte to be detected, in particular at the end of the analysis method, and/or
the reading of the signal produced by at least one detection marker of a detection ligand of an analyte to be detected on a reading grid defined from the location of the signal produced by said resistant control marker(s).

The reading of the signal produced by at least one detection marker of a detection ligand of an analyte to be detected is therefore done on a reading grid defined from the location of the signal produced by said resistant control marker(s) and detected at the end of the analysis method.

The present invention in particular relates to the use of at least one resistant control marker in at least one spot intended to detect an analyte to secure a method for detecting at least one analyte in a sample or at least one sample, characterized in that it comprises:
checking the quality of said spot, after said spot has been placed in the presence of the sample and at least one detection ligand of an analyte to be detected coupled with an indirect detection marker, a reporter (also called first reporter) of said indirect detection marker, optionally a second reporter of an indirect detection marker coupled to said first reporter, and/or
the reading of the signal produced by at least one detection marker of a detection ligand of an analyte to be detected on a reading grid defined from the location of the signal produced by said resistant control marker(s).

The present invention particularly relates to the use as defined above, characterized in that the quality control of the spot comprises or consists of checking the presence, location and/or integrity of the spot.

The reading grid indicates the zone(s) of the compartment in which the signal produced by the detection marker(s) of a detection ligand of an analyte must be read.

Other features and advantages of the invention will better emerge through the following examples, provided as an illustration and non-limitingly.

EXAMPLES

Example 1: Example Method for Selecting a Resistant Control Marker

Materials and Method

Within each well of a polystyrene microplate (Greiner, Germany) are deposited, well by well, drops of 500 nl of a fluorophore solution in the buffer traditionally used for spotting of antigens or antibodies. The following fluorophores are used in this example: Atto 633-carboxylic acid (i.e., Atto 633-COOH or Atto 633) (supplier: ATTO-TEC; Germany), Atto 633-amine (i.e., Sérivé amine from Atto 633) (supplier: ATTO-TEC; Germany), Dye 634-carboxylic acid (i.e., Dye 634-COOH or Dye 634) (supplier: Dyomics, Germany), Dye 634-amine (i.e., Sérivé amine from Dye 634) (supplier: Dyomics, Germany), Dye 630-amine (i.e., Sérivé amine from Dye 630) (supplier: Dyomics, Germany), APC (Allophycocyanin) (supplier Febico; Taiwan), B-Phycoerythrin (Febico; Taiwan). The bottom of each well of these microplates has molecule adsorption capacities known in themselves by those skilled in the art. The surface of each well thus obtained is saturated with a saturation solution known in itself by those skilled in the art; the wells are filled with the saturation solution, the saturation solution is removed and the wells are next dried; after a rehydration step of these wells, a substrate solution containing the luminol (ELISTAR ETA C Ultra ELISA (Cyanagen, Italy) (cf. example 2) is then added at a rate of 50 µL/well. The fluorescence images are done at the different steps of the protocol described above (i.e., after the steps for depositing drops, saturation, drying, rehydration, and after adding the substrate solution containing the luminol), by using the Chemidoc™ MP System (Bio-Rad) having the appropriate filters for fluorophores.

Results

Figure 1:
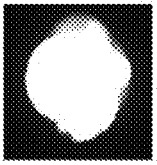
FIG. 1: Use of different fluorophores and resulting fluorescence images in different steps of the protocol described in example 1.

FIG. 1 describes the use of different fluorophores and resulting images in different steps of the protocol described above.

The fluorescence obtained with the 4 fluorophores is fully visible at the end of the deposition of the drops on the plate. This fluorescence persists for the Atto 633-amine, the allophycocyanin and the B-Phycoerythrin after elimination of the saturation solution (cf. spots after saturation). It also persists after adding the substrate solution containing the luminol for the Atto 633-amine and for the B-Phycoerythrin, very weakly for the allophycocyanin. Similar results are obtained with the Dye 634-amine and the Dye 630-amine (results not shown). Conversely, no residual fluorescence is visible at the end of the washing step with the Dye 634-carboxylic acid and a fortiori after adding the substrate solution, as well as for the Atto 633-carboxylic acid (results not shown).

Thus, the Atto 633-amine, the Dye 634-amine, the Dye 630-amine and the B-Phycoerythrin are resistant control markers according to the present invention.

Furthermore, as illustrated below in example 2, the Dye 634 coupled to the BSA is also a resistant control marker according to the invention.

Example 2: Absence of Impact of the Presence of a Resistant Control Fluorophore on the Detection of an Analyte of Interest Materials and Method (i) Preparation of the Microplate Within each well of a polystyrene microplate (Greiner, Germany), a spotter robot is used to deposit 50 nL drops of a solution containing the capture ligand(s) as well as a fluorophore selected using the method described in the application in rows.

The capture ligand solution can be:
either an antigen or mixture of antigens able to be made up of a recombinant protein associated with one or more synthetic peptides as part of an antibody detection test,
or an antibody or mixture of antibodies against the sought marker in the case of an antigen detection test.

These capture ligand solutions contain the selected fluorophore, for example the Atto 633-amine (Atto-tec, Germany) or a Dye 634-BSA complex, obtained using a protocol known by those skilled in the art from Dye 634 (Dyomics, Germany) in NHS-ester (N-Hydroxysuccinimide ester) form coupled with the BSA; these fluorophores are added at the appropriate dose, determined for each one; for the Dye 634-BSA, the indicated dose corresponds to the concentration of the Dye 634-BSA complex. The bottom of each well of these microplates has adsorption capacities for these different proteins known in themselves by those skilled in the art.

The spots thus obtained are saturated with a saturation solution known in itself by those skilled in the art. The plates are next dried.

(ii) Implementation of the Analysis Method

Description of the various elements used during the implementation of the analysis method:

Reporter
  The Streptavidin-POD (S-POD) reporter is streptavidin (Roche, Germany) coupled with Peroxidase (Roche Germany) according to the method described by Nakane and Kawaoi [J Histochem Cytochem (1974) Vol. 22, No. 12. pp. 1084-1091] known in itself by those skilled in the art.
Wash Solution
  Tris 10 mM buffer solution, pH 7.4, containing: NaCl 218 mM, Tween 20™ (trademark of the company Sigma) at 0.1%, Proclin 300™ (trademark of the company Supelco) at 0.002%.
Developing Substrate
  The ELISTAR ETA C Ultra ELISA developing substrate (Cyanagen, Italy) is made up of two solutions: XLSE024L Luminol enhancer solution (A) and XLSE024P Peroxide solution (B).

Description of the Different Steps Carried Out:

The test protocol comprises the following steps:

Step 1:
1. In each well of a microplate (comprising the spots) are distributed:
    40 µl of sample: the sample can for example be a serum or a control sample
    40 µl of diluent
2. The mixture is incubated for 40 minutes at 37° C. with agitation.
3. Three successive washes with at least 300 µl of wash solution are done.
4. Next, an incubation step is done in the presence of the detection ligand, then washing under the same conditions as point 3.
5. Then, an incubation step of the reporter, then washing.
6. Lastly, a final developing step, including the addition of 25 µl of each of developing substrate solutions B and A.

7. The mixture is incubated for 1 minute at 37° C. with agitation.
8. The readings are done with a Chemidoc™ reader to measure the fluorescence and a Qview™ reader to measure the chemiluminescence. The results of the readings are processed directly by an image analysis system and recorded in Relative Light Units (RLU); also, Relative Fluorescence Intensity (RFI).

Results

Each datum corresponds to an average of a triplicate; the fluorescence values correspond to the fluorescence signal level after deducting the background noise.

Results Obtained with the Atto 633-Amine Fluorophore Added into the Specific Antibody solution of the marker of interest to be detected;

TABLE 1

Impact of the presence of the Atto 633-amine fluorophore on the detection of the analyte for different fluorophore doses. E1, E2 and E3 are positive samples, containing the antigen to be detected, at different positivity levels.

| | | Atto 633-amine fluorophore | |
|---|---|---|---|
| Sample | Composition of the deposit solutions | Chemiluminescence signal RLU | Comparison of the chemiluminescence signal relative to the absence of fluorophore |
| E1 | Antibody without fluorophore | 1489.5 | reference |
| | Antibody + Fluo 0.1 µg/ml | 1726 | 16% |
| | Antibody + Fluo 0.35 µg/ml | 1703 | 14% |
| | Antibody + Fluo 1.2 µg/ml | 1377 | −8% |
| | Antibody + Fluo 2.5 µg/ml | 1438 | −3% |
| | Antibody + Fluo 5 µg/ml | 1210 | −19% |
| E2 | Antibody without fluorophore | 4651 | reference |
| | Antibody + Fluo 0.1 µg/ml | 5033 | 8% |
| | Antibody + Fluo 0.35 µg/ml | 4861 | 5% |
| | Antibody + Fluo 1.2 µg/ml | 3679 | −21% |
| | Antibody + Fluo 2.5 µg/ml | 4115 | −12% |
| | Antibody + Fluo 5 µg/ml | 3779 | −19% |
| E3 | Antibody without fluorophore | 2188 | reference |
| | Antibody + Fluo 0.1 µg/ml | 2117 | −3% |
| | Antibody + Fluo 0.35 µg/ml | 2264 | 3% |
| | Antibody + Fluo 1.2 µg/ml | 1650 | −25% |
| | Antibody + Fluo 2.5 µg/ml | 1479 | −32% |
| | Antibody + Fluo 5 µg/ml | 1226 | −44% |

The results shown in table 1 show the absence of impact of the presence of the Atto 633-amine fluorophore on the detection of the analyte for fluorophore doses of 0.35 µg/ml or less. The calculation of the detection limit of the analyte shows the absence of impact of the presence of the fluorophore up to a dose of 1.2 µg/ml. The presence of the capture ligands only very slightly modifies the fluorescence (cf. table 2), which remains very significant and fully detectable at the end of the analysis.

TABLE 2

Impact of the presence of capture ligands on the fluorescence signal (case of the Atto 633-amine fluorophore). E1 and E3 are positive samples, containing the antigen to be detected, at different positivity levels. N1 is a negative sample, not containing the antigen to be detected. 'Fluo' stands for Fluorophore.

| | | Atto 633-NH2 fluorophore | | |
|---|---|---|---|---|
| Sample | Composition of the deposit solutions | Fluorescence signal RLU | Chemiluminescence signal RLU | Comparison of the fluorescence signal relative to the absence of markers of interest |
| E1 | Fluorophore alone 0.1 µg/ml | 26843 | 54 | −21% |
| | Antibody + Fluo 0.1 µg/ml | 21158 | 1726 | |
| E3 | Fluorophore alone 0.1 µg/ml | 29039 | 56 | −31% |
| | Antibody + Fluo 0.1 µg/ml | 20021 | 2117 | |
| N1 | Fluorophore alone 0.1 µg/ml | 24999 | 57 | −29% |
| | Antibody + Fluo 0.1 µg/ml | 17641 | 49 | |

Results Obtained with the Dye 634-BSA Fluorophore Added into the Specific Antibody Solution of the Marker of Interest to be Detected:

The results shown in table 3 show the absence of impact of the presence of the Atto 634-BSA on the detection of the analyte for fluorophore doses of 6 µg/ml or less, this dose being compatible with the detection of the fluorescence at the end of analysis and the implementation of the data processing method as described in the present application.

TABLE 3

Impact of the presence of the Atto Dye 634-BSA fluorophore on the detection of the analyte for different fluorophore doses. E1, E2 and E3 are positive samples, containing the antigen to be detected, at different positivity levels. 'Fluo' stands for Fluorophore.

| | | Dye 634-BSA fluorophore | |
|---|---|---|---|
| Sample | Composition of the deposit solutions | Chemiluminescence signal RLU | Comparison of the chemiluminescence signal relative to the absence of fluorophore |
| E1 | Antibody without fluorophore | 1856 | reference |
| | Antibody + Fluo 3 µg/ml | 1716 | −8% |
| | Antibody + Fluo 6 µg/ml | 1782 | −4% |
| | Antibody + Fluo 12 µg/ml | 1562 | −16% |
| | Antibody + Fluo 25 µg/ml | 1379 | −26% |
| | Antibody + Fluo 50 µg/ml | 1297 | −30% |
| E2 | Antibody without fluorophore | 5576 | reference |
| | Antibody + Fluo 3 µg/ml | 5471 | −2% |
| | Antibody + Fluo 6 µg/ml | 4908 | −12% |
| | Antibody + Fluo 12 µg/ml | 4133 | −26% |
| | Antibody + Fluo 25 µg/ml | 4231 | −24% |
| | Antibody + Fluo 50 µg/ml | 4629 | −17% |
| E3 | Antibody without fluorophore | 2183 | reference |
| | Antibody + Fluo 3 µg/ml | 2397 | 10% |
| | Antibody + Fluo 6 µg/ml | 2184 | 0% |
| | Antibody + Fluo 12 µg/ml | 1714 | −21% |
| | Antibody + Fluo 25 µg/ml | 1445 | −34% |
| | Antibody + Fluo 50 µg/ml | 1347 | −38% |

Results Obtained with the Atto 633-Amine Fluorophore Added into the Antibody Solution Corresponding to the Antibodies to be Detected:

The results shown in table 4 show the absence of impact of the presence of the Atto 633-amine fluorophore on the detection of the analyte for the fluorophore dose of 0.1 µg/ml or less. The presence of capture ligands (cf. table 5) modifies the fluorescence, but the signal remains very significant, fully detectable at the end of analysis and usable to implement the data processing method as described in the present application.

TABLE 4

Impact of the presence of the Atto 633-amine fluorophore on the detection of the analyte for different fluorophore doses. Samples S1 and S2 are positive samples, containing antibodies reacting selectively and respectively relative to 2 types of antigens used in mixture: recombinant protein or synthetic peptide. 'Fluo' stands for Fluorophore.

| | | Atto 633-amine fluorophore | |
|---|---|---|---|
| Sample | Composition of the deposit solutions | Chemiluminescence signal RLU | Comparison of the chemiluminescence signal relative to the absence of fluorophore |
| S2 | Antigens without fluorophore | 410 | reference |
| | Antibody + Fluo 0.1 µg/ml | 355 | −13% |
| | Antigens + Fluo 0.35 µg/ml | 351 | −14% |
| | Antigens + Fluo 1.2 µg/ml | 366 | −11% |
| | Antigens + Fluo 2.5 µg/ml | 330 | −20% |
| | Antigens + Fluo 5 µg/ml | 247 | −40% |

TABLE 4-continued

Impact of the presence of the Atto 633-amine fluorophore on the detection of the analyte for different fluorophore doses. Samples S1 and S2 are positive samples, containing antibodies reacting selectively and respectively relative to 2 types of antigens used in mixture: recombinant protein or synthetic peptide. 'Fluo' stands for Fluorophore.

| | | Atto 633-amine fluorophore | |
|---|---|---|---|
| Sample | Composition of the deposit solutions | Chemiluminescence signal RLU | Comparison of the chemiluminescence signal relative to the absence of fluorophore |
| S1 | Antigens without fluorophore | 1638 | reference |
| | Antibody + Fluo 0.1 µg/ml | 1547 | −6% |
| | Antigens + Fluo 0.35 µg/ml | 1215 | −26% |
| | Antigens + Fluo 1.2 µg/ml | 1261 | −23% |
| | Antigens + Fluo 2.5 µg/ml | 1253 | −24% |
| | Antigens + Fluo 5 µg/ml | 1194 | −27% |

TABLE 5

Impact of the presence of capture ligands on the fluorescence signal (case of the Atto 633-amine fluorophore). Samples S1 and S2 are positive samples, containing antibodies reacting selectively and respectively relative to 2 types of antigens used: recombinant protein or synthetic peptide. N2 is a negative sample, not containing antibodies recognizing the antigen to be detected. 'Fluo' stands for Fluorophore.

| | | Atto 633-amine fluorophore | | |
|---|---|---|---|---|
| Sample | Composition of the deposit solutions | fluorescence signal RLU | Chemiluminescence signal RLU | Comparison of the fluorescence signal relative to the absence of markers of interest |
| N2 | Fluorophore alone 0.1 µg/ml | 70881 | 70 | −47% |
| | Antigens + Fluo 0.1 µg/ml | 37781 | 67 | |
| S2 | Fluorophore alone 0.1 µg/ml | 72852 | 93 | −45% |
| | Antigens + Fluo 0.1 µg/ml | 39877 | 355 | |
| S1 | Fluorophore alone 0.1 µg/ml | 73721 | 117 | −47% |
| | Antigens + Fluo 0.1 µg/ml | 39096 | 1547 | |

Results Obtained with the Dye 634-BSA Fluorophore Added into the Antibody Solution Corresponding to the Antibodies to be Detected:

TABLE 6

Impact of the presence of the Atto Dye 634-BSA fluorophore on the detection of the analyte for different fluorophore doses. The sample S1 is a sample containing antibodies reacting with respect to the recombinant protein used. 'Fluo' stands for Fluorophore.

| | | Dye 634-BSA fluorophore | |
|---|---|---|---|
| Sample | Composition of the deposit solutions | Chemiluminescence signal RLU | Comparison of the chemiluminescence signal relative to the absence of fluorophore |
| S1 | Antigens without fluorophore | 1066 | reference |
| | Antigens + Fluo 3 µg/ml | 1218 | 14% |
| | Antigens + Fluo 6 µg/ml | 1003 | −6% |
| | Antigens + | 1277 | 20% |
| | Fluo 12 µg/ml | | |
| | Antigens + Fluo 25 µg/ml | 1291 | 21% |
| | Antigens + Fluo 50 µg/ml | 1247 | 17% |

The results shown in table 6 show the absence of impact of the presence of the Dye 634-BSA fluorophore on the detection of the analyte irrespective of the fluorophore dose. The fluorescence signal obtained at the end of analysis is fully detectable and usable to implement the data processing method as described in the present application.

Example 3: Use of a Resistant Control Marker to Secure a Method for Detecting at Least One Analyte in a Sample Materials and Method
(i) Preparation of the Microplate Within each well of a polystyrene microplate (Greiner, Germany), a spotter robot is used to deposit 50 nL drops of a solution containing the capture ligand(s) as well as a fluorophore selected using the method described in the application in rows.

The capture ligand solution can be:
- either an antigen or mixture of antigens able to be made up of a recombinant protein associated with one or more synthetic peptides as part of an antibody detection test,
- or an antibody or mixture of antibodies against the sought marker in the case of an antigen detection test.

These capture ligand solutions contain the selected Atto 633-amine fluorophore (Atto-tec, Germany) at the appropriate dose comprised between 0.1 to 0.5 µg/mL. The bottom of each well of these microplates has adsorption capacities for these different proteins known in themselves by those skilled in the art.

The spots thus obtained are saturated with a saturation solution known in itself by those skilled in the art. The plates are next dried.

(ii) Implementation of the Analysis Method
Description of the Various Elements Used During the Implementation of the Analysis Method:

I. Reporter

The Streptavidin-POD (S-POD) reporter is streptavidin (Roche, Germany) coupled with Peroxidase (Roche Germany) according to the method described by P. Nakane and A. Kawaoi [J Histochem Cytochem (1974) Vol. 22, No. 12. pp. 1084-1091] known in itself by those skilled in the art.

II. Diluents
a) Diluent Step 1
Tris buffer solution 50 mM, pH 7.5, containing: NaCl 150 mM, EDTA 20 mM, mouse IgG (Meridian) at 500 µg/mL, Cow's milk (100% skim) at 15%, Sheep serum at 10%, NaN3 at 0.095%.

b) Diluent of Conjugates 1
Tris buffer solution 50 mM, pH 7.5, containing: NaCl 150 mM; EDTA 20 mM, Chaps 0.1%, Glycerol 10%, NaN3 at 0.095%.

c) Diluent of Conjugates 2
Citrate buffer solution 50 mM, pH 6.7, containing: NaCl 150 mM, EDTA 5.6 mM, Triton at 2%, Sheep serum at 10%, mouse IgG 500 µg/mL, Proclin 300™ (trademark of the company Supelco) at 0.5%, cow's milk (100% skim) at 15%, Glycerol 10%. NaN3 at 0.095%.

d) Diluent of the Streptavidin-POD Reporter
Citrate buffer solution 50 mM, pH 6.7, containing: NaCl 2053 mM, Tween 20™ (trademark of the company Sigma) at 0.5%, Proclin 300™ (trademark of the company Supelco) at 0.5%, cow's milk (100% skim) at 7%, Glycerol 20%.

e) Wash Solution
Tris 10 mM buffer solution, pH 7.4, containing: NaCl 218 mM, Tween 20™ (trademark of the company Sigma) at 0.1%, Proclin 300™ (trademark of the company Supelco) at 0.002%.

f) Developing Substrate
The ELISTAR ETA C Ultra ELISA developing substrate (Cyanagen, Italy) is made up of two solutions: XLSE024L Luminol enhancer solution (A) and XLSE024P Peroxide solution (B).

III. Reaction Dishes
The immunological reactions take place in 96-well microplates (Greiner, Germany) made from polystyrene having a maximum volume of 392 µL per well.

IV. Samples
The negative samples (serum or plasma) used come from the French blood agency in Lille.

V. Optical Bench
The optical bench used is made up of the following elements:
- a lighting system emitting red light centered on the wavelength of 620 nm and assembled such that it illuminates the lower face of the microplate homogenously,
- a telecentric objective produced to make it possible to image the entire surface of the microplate,
- a filter wheel inserted between the output lens of the telecentric objective and the camera,
- a camera having the ability to produce images with exposure times comprised between 0.001 second and 250 seconds,
- a support chassis that supports and positions all of the elements, including the microplate.

The optical bench is studied and assembled such that it takes the images from the lower face of the microplate. The development of the objective is done such that the inner face of the microplate wells is clear.

The filter wheel is able to have two different filters:
- a filter centered on the wavelength of 680 nm making it possible to allow only the signal corresponding to the light emitted by the fluorophore to pass,
- a filter making it possible to allow all of the wavelengths comprised between 400 nm and 700 nm to pass.

Description of the different steps carried out:
The test protocol comprises the following steps:
Step 1:
1. In each well of a microplate (comprising the spots) are successively distributed:
+20 µl of diluent step 1
+20 µl of diluent of conjugates 1 comprising the detection ligands of the analytes to be assayed from the first step
+40 µl of sample
2. The mixture is incubated for 40 minutes at 37° C. with agitation.
3. Three successive washes with at least 400 µl of wash solution are done.
Step 2:
4. Distributed in each reaction well is 50 µl of diluent of conjugates 2 containing the detection ligands of the analytes to be assayed from the second step.
5. The mixture is incubated for 15 minutes at 37° C. with agitation.
6. The wash steps (idem point 3) are carried out.
Step 3:
7. 50 µL of the S-POD reporter is distributed in each reaction well.
8. The mixture is incubated for 15 minutes at 37° C. with agitation.
Step 4:
9. 25 µL of developing solution "B" is distributed in each reaction well.

10. 25 µL of developing solution "A" is distributed in each reaction well.

10. The mixture is incubated for 1 minute at 37° C. with agitation.

11. The acquisition of the fluorescence signal is done for 10 seconds.

12. The acquisition of the luminescence signal is done for 180 seconds.

Results

A) Persistence of the Resistant Control Marker After an Analysis Method.

Figure 2:
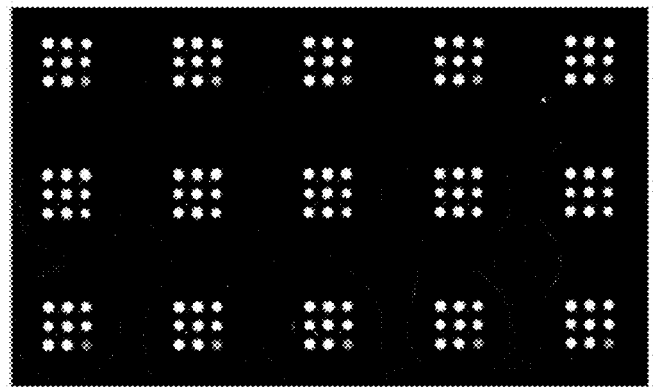
FIG. 2: Acquisition of the fluorescence signal of 12 wells comprising 9 spots at the end of an analysis method according to the invention.

The fluorescence signal of the resistant control marker of each of the 9 spots present in the 12 wells is clearly identifiable and fully measurable at the end of the analysis method in FIG. 2.

B) Importance of redefining the reading grid at the end of the analysis method: comparison of the regions of interest obtained by fluorescence by defining the reading grid relative to the theoretical positions versus by defining the reading grid from the signal emitted by fluorescence by the resistant control marker.

Figure 3:
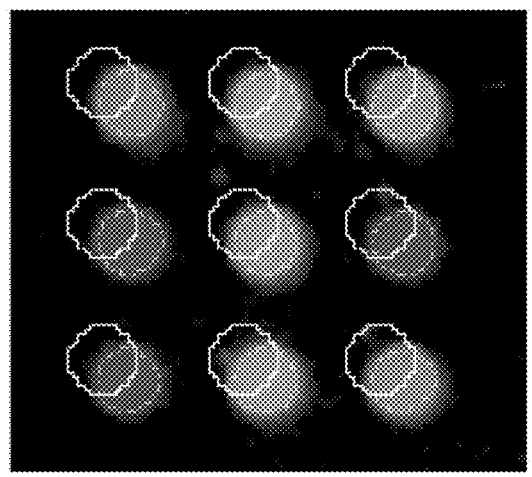
FIG. 3: Fluorescence image: Comparison of the theoretical reading grid (solid white circles) relative to the actual position of the spots by fluorescence (dotted white circles) based on the signal produced by the resistant control marker.

In FIG. 3, the solid white circles show the theoretical position of the spots, the dotted white circles showing the detected actual position. The spots are clearly shifted relative to their expected theoretical position.

This image demonstrates the relevance of the method, which always makes it possible to target the position of the detected actual spot through the resistant control marker, which does not cause errors in the reading of the signal emitted by the detection marker of the detection ligand of the analyte.

C) Importance of redefining the reading grid at the end of the analysis method: comparison of the regions of interest obtained by chemiluminescence by defining the reading grid relative to the theoretical positions versus by defining the reading grid from the signal emitted by fluorescence by the resistant control marker.

Figure 4:
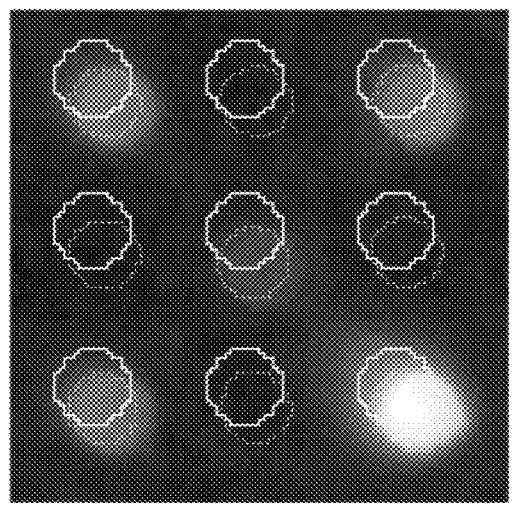
FIG. 4: Chemiluminescence image: Improvement of the accuracy of the analysis method by defining the reading grid on the actual position of the spots detected through the resistant control marker (dotted line), versus the theoretical position grid (solid lines).

The location of the actual spots (dotted lines) was obtained based on signals produced by the resistant control marker and applied on the acquisition image of the signals of the detection marker of a ligand of the analyte by chemiluminescence shown here in FIG. 4. The theoretical positioning of the spots is indicated in solid lines and clearly shows a shift relative to the actual position.

The comparison between the median values in chemiluminescence of the pixels situated under the expected theoretical positions (solid lines) and the actual detected positions (dotted lines) by fluorescence is shown in table 7.

TABLE 7

Signal measured from the analysis of the theoretical presence region of a spot versus signal measured from the analysis of the actual position region of that same spot

|  | Spot 1 (top left) | Spot 3 (top right) | Spot 5 (middle) | spot 9 (bottom right) |
| --- | --- | --- | --- | --- |
| Theoretical position | 319 | 301 | 58 | 3387 |
| Actual position | 689 | 693 | 138 | 5233 |

The analysis of the region containing a spot producing the signal provides significantly higher results than the theoretical presence region of that same spot. The quantification of the signal and the accuracy of the results obtained are therefore improved by basing oneself on the detected actual positioning grid owing to the resistant control marker.

D) Example of deteriorated spot after an analysis method and that could have yielded a false result without verification of the integrity of the spots.

Figure 5:
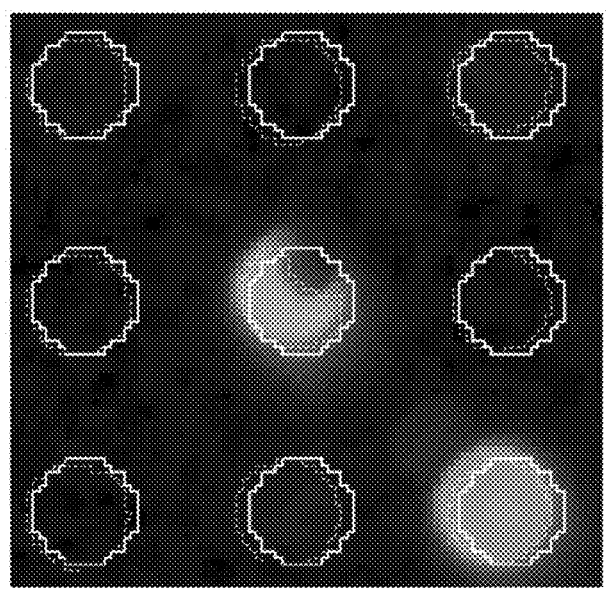
FIG. 5: Chemiluminescence image: Improvement of the accuracy of the analysis method by verifying the integrity of the spots detected before validating the results.
Figure 6:
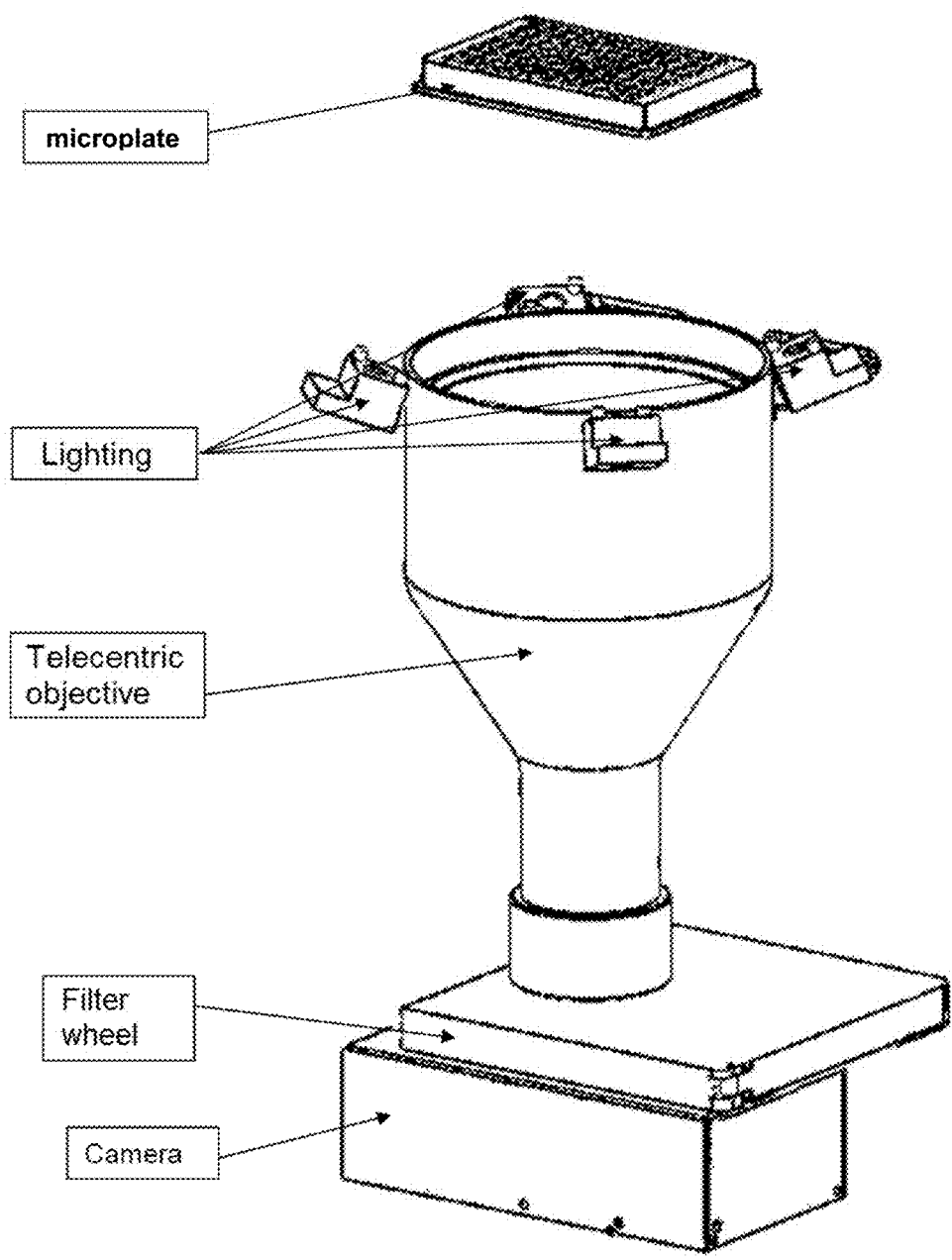
FIG. 6: Diagram of an optical bench comprising a lighting system, a telecentric objective, a filter wheel, said telecentric objective being coupled on its output lens to the filter wheel, and a camera.

The location of the actual spots (dotted lines) was obtained based on signals produced by the resistant control marker and applied on the acquisition image of the signals of the detection marker of a ligand of the analyte by chemiluminescence shown here (cf. FIG. 5). The theoretical positioning of the spots is indicated in solid lines.

In the image (cf. FIG. 5), the spot located at the center of the well is deformed. The broken white line surrounding it shows that the software detected the actual shape of the spot, which makes it possible to analyze its integrity before validating the results yielded. In this case, the circularity perimeter of the actual shape of the spot makes it possible to eliminate this spot and not yield a false analysis value.

The invention claimed is:

1. A method for detecting at least one analyte in at least one sample comprising the following steps:
    a) placing a sample to be analyzed into a compartment of a solid support, said compartment comprising one or more spots comprising at least one resistant control marker and at least one capture ligand of an analyte,
    b) placing at least one detection ligand of said analyte into said compartment, said detection ligand of said analyte being coupled to a direct or indirect detection marker,
    c) when said at least one detection ligand of said analyte is coupled to said indirect detection marker, placing a first reporter of said indirect detection marker into said compartment,
    d) when the reporter used in step c) is coupled to said indirect detection marker, placing a second reporter of the indirect detection marker coupled to said first reporter used in step c) into said compartment,
    e) detecting at least one signal produced by said at least one resistant control marker in said compartment,
    f) defining at least one reading grid from the location of at least one signal detected in step e),
    g) detecting a signal produced by said at least one detection marker of said detection ligand of said analyte, and
    h) reading the signal detected in step g) on the reading grid defined in step f).

2. The method according to claim 1, wherein, in step g), the signal produced by said at least one detection marker of said detection ligand of said analyte is a luminescent signal.

3. The method according to claim 1, wherein said at least one resistant control marker(s) is a fluorophore.

4. The method according to claim 3, wherein said at least one resistant control marker(s) is a fluorophore, wherein an excitation spectrum of the fluorophore does not overlap with the emission spectrum of the signal emitted by or corresponding to the detection marker of said detection ligand(s) of said analyte and wherein an emission spectrum of the fluorophore does not overlap, or partially overlaps, with the emission spectrum of or corresponding to the detection marker of said detection ligand(s) of said analyte.

5. The method according to claim 1, wherein:
    in step g), the signal produced by the at least one detection marker of said detection ligand of said analyte is the light emitted by a chemiluminescent compound obtained by reaction of a peroxidase with the luminol, an analogue of the luminol and/or of a derivative of the luminol or an analogue of the luminol, and in step e), the signal produced by the resistant control marker(s) is a light emitted outside the wavelengths from 375 to 550 nm.

\* \* \* \* \*